(12) United States Patent
Shapiro et al.

(10) Patent No.: US 8,110,083 B1
(45) Date of Patent: Feb. 7, 2012

(54) ARBITRARY AND SIMULTANEOUS CONTROL OF MULTIPLE OBJECTS IN MICRO-FLUIDIC SYSTEMS

(75) Inventors: Benjamin Shapiro, Washington, DC (US); Satej V. Chaudhary, Greenbelt, MD (US); Michael D. Armani, Dayton, MD (US); Roland Probst, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 12/651,742

(22) Filed: Jan. 4, 2010

Related U.S. Application Data

(63) Continuation of application No. 10/933,357, filed on Sep. 3, 2004, now Pat. No. 7,651,598.

(51) Int. Cl.
*C25B 9/00* (2006.01)

(52) U.S. Cl. ........ 204/616; 204/450; 204/456; 204/466; 204/600; 204/606

(58) Field of Classification Search .................. 204/450, 204/456, 466, 600, 606, 616
See application file for complete search history.

(56) References Cited

U.S. PATENT DOCUMENTS

| | | |
|---|---|---|
| 6,977,033 B2 | 12/2005 | Becker et al. |
| 7,010,391 B2 | 3/2006 | Handique et al. |
| 2002/0092767 A1 | 7/2002 | Bjornson et al. |
| 2003/0075444 A1 | 4/2003 | Huang et al. |

OTHER PUBLICATIONS

Fu, A., et al.; "Accelerated Articles. An Integrated Microfabricated Cell Sorter"; Analytical Chemistry; 2002; 74; 2451-2457.
Cho, S.K., et al., "Creating, Transporting, Cutting, and Merging Liquid Droplets by Electrowetting-Based Actuation for Digital Microfluidic Circuits," J. of Microelectrochemical Sys., vol. 12, No. 1, Feb. 2003, pp. 70-80.
Reznik, D.S., "The Universal Planar Manipulator," Dissertation— University of California at Berkley, Fall 2000.

*Primary Examiner* — Alexa D. Neckel
*Assistant Examiner* — Nicholas A. Smith
(74) *Attorney, Agent, or Firm* — Rosenberg, Klein & Lee

(57) ABSTRACT

In a microfluidic device, respective motion of a plurality of objects along corresponding trajectories is achieved by determining a force field, such as an underlying fluid flow which, when applied to the plurality of object, moves each object along its corresponding trajectory. The force field is a linear superposition of a subset of all force fields supported by the physical characteristics of the microfluidic device. Once the fields have been ascertained, a plurality of actuation signals corresponding to the fields is applied to actuators installed on the microfluidic device to cause the force on each object. By implementing a feedback structure, corrections for positional errors may be made by computing a corrective force for each object and adjusting the actuation signals appropriately thereto.

26 Claims, 16 Drawing Sheets

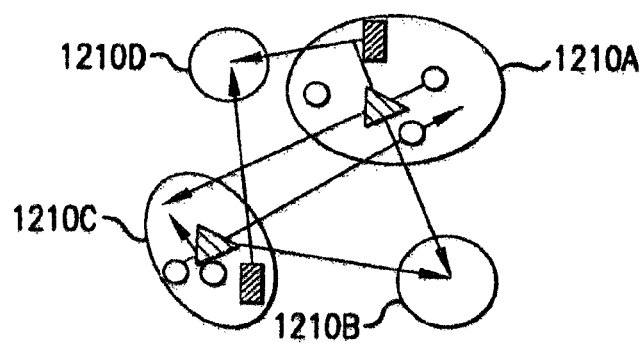
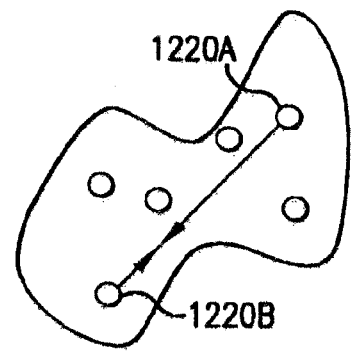
FIG.12A  FIG.12B
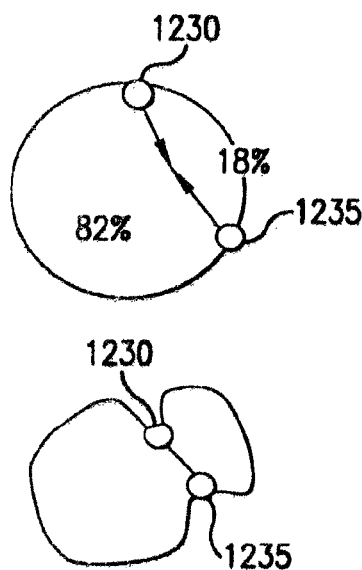
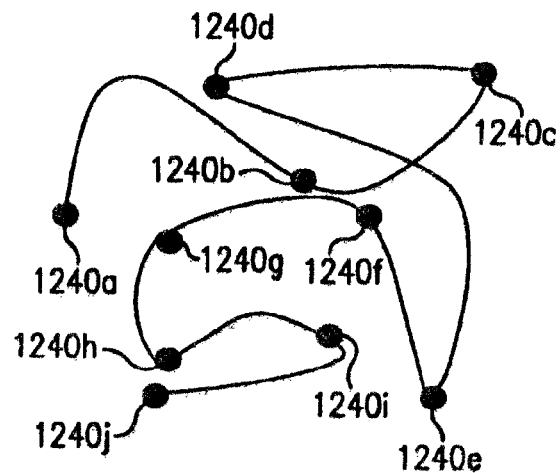
FIG.12C  FIG.12D

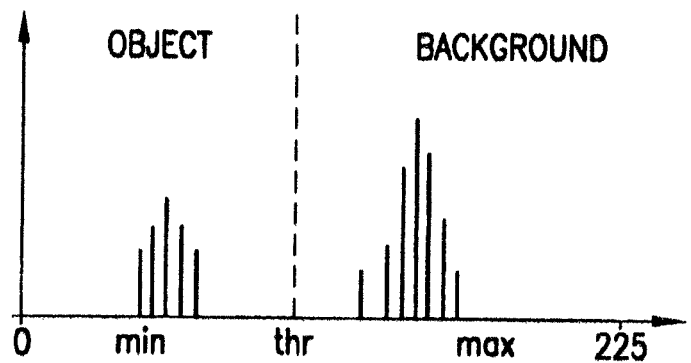
FIG. 15
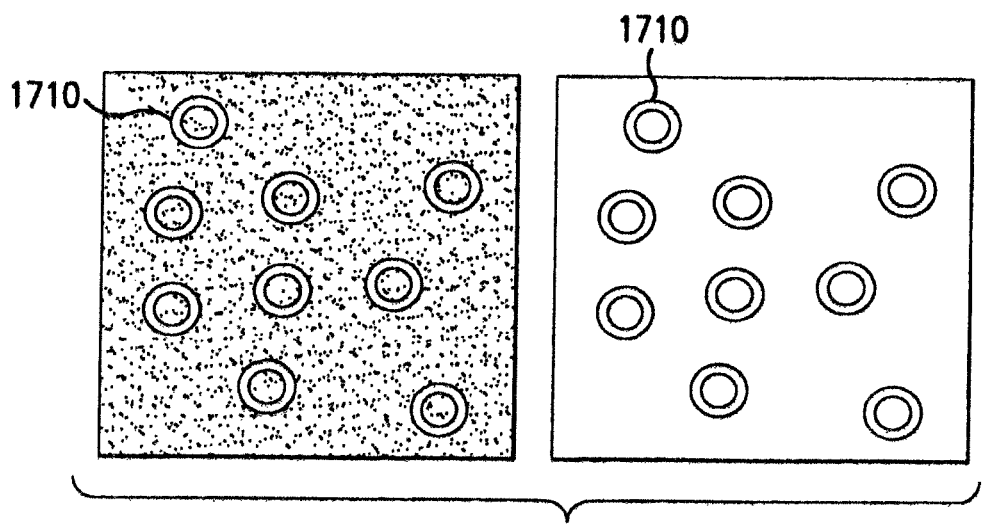
FIG. 16
FIG. 17

ARBITRARY AND SIMULTANEOUS CONTROL OF MULTIPLE OBJECTS IN MICRO-FLUIDIC SYSTEMS

CROSS-REFERENCE TO RELATED APPLICATION

This application is a continuation of U.S. patent application Ser. No. 10/933,357, now U.S. Pat. No. 7,651,598.

STATEMENT REGARDING FEDERALLY SPONSORED RESEARCH

This invention was made with support of the United States Government. The United States Government has certain rights in the invention.

BACKGROUND OF THE INVENTION

1. Field of the Invention

The invention described herein is directed to the manipulation of multiple objects suspended in fluids within microfluidic devices through the application of complex force fields. More specifically, the present invention is a method for determining and subsequently applying a set of signals to one or more actuators on a microfluidic device so as to respectively apply a corresponding force on each of one or more objects contained therein to thereby manipulate the position, velocity, shape, orientation, and/or distribution thereof.

2. Description of the Prior Art

Microfabrication techniques have been used for over a decade to produce a variety of submillimeter mechanical structures. For example, the new fabrication techniques have led the way to the production of Micro-Electro-Mechanical Systems (MEMS) in which microscopic machinery, sensors, actuators, and electronic circuitry are assembled on, and in many cases etched from, a common substrate, such as silicon. Many of these micromachined devices have enjoyed a wide range of applicability in such fields as chemical and biological research.

In certain technological fields, such as the aforementioned chemical and biological research, the physical scale of certain domains of interest have motivated the development of sophisticated equipment capable of manipulating microscopic objects, both individually and in selected groups. One device widely used in this area is the optical tweezer (also known as laser tweezers) which uses laser light to manipulate objects of molecular size scales. Optical tweezers create an optical trap on an object through light scattering forces and light intensity gradient forces of a focused laser beam. The forces combine to hold the object in the center of the focused laser spot. The trapped object may be repositioned by moving the focused laser spot as desired.

Optical tweezers are effective in manipulating certain types of objects, but suffer several shortcomings which prevent their implementation in a wider range of applications. Optical tweezers can be used to manipulate particles, provided there is a difference in the index of refraction of the particle and that of the surrounding medium, but have yet to be used effectively to redistribute fluids. Manipulation of fluids on a microscopic scale has become a useful method in delivering chemical agents to individual cells to observe how the cells react thereto.

Another shortcoming of optical tweezers is that they are large and generally expensive pieces of equipment. In typical applications, a laser tweezer will consist of one or more lasers, a microscope, and high-quality focusing optics to produce each optical trap.

Manipulation of submillimeter objects by electrophoresis and other methods using an applied electric field have been used for many years. Electrophoresis has been widely used for separating and sorting particles into bands in accordance with particle size and inherent electric charge. Gel electrophoresis, for example, whereby an electric field is applied to molecules suspended in a porous gel, is used in the field of genetics for DNA profiling. However; while electrophoresis is useful for applying a force on certain particles, such as molecules, the process is not operative on objects immovable by an electric field, such as objects made of a dielectric material. Additionally, electrophoresis may be used to sort particles according to a charge/size ratio into sorting bins located along a straight path, but does not provide a means for steering the objects toward alternative locations not on the path.

Sorting of minute particles is a prevalent requirement in many research and biochemical fields, and many means for performing this task are widely available. For example, one common application passes a stream of particles suspended in an electrolyte through a small aperture over which an electric field is applied. A particle in the aperture displaces an amount of electrolyte equal to its own volume. In accordance with the Coulter principle, the volume displaced changes the impedance of the aperture and is measured as a voltage pulse, the height of which is proportional to the volume of electrolyte displaced, i.e., the volume of the particle. The particles may then be sorted by size by deflecting different sized particles into a corresponding sorting location or bin, by some mechanism such as an optical tweezer. The Coulter particle sorter illustrates the benefits of device implementation on a micromachined platform, i.e., to measure a change in impedance in a channel or aperture caused by the presence of a microscopic particle, the channel or aperture is required to be formed on a size scale comparable with the size of the particle.

An illustrative example of another cell sorting device constructed by micromachined techniques is provided by the journal article, "An Integrated Microfabricated Cell Sorter," by Anne Fu, et al. (Analytical Chemistry, Vol. 74, No. 11, Jun. 1, 2002). The referenced cell sorter implements a network of microvalves and micropumps for controlling the movement of cells suspended in a fluid after the classification thereof by controlling the surrounding fluid flow. Cells within the device are classified by means of fluorescence of the cell resulting from excitation by an argon laser. Various valves and pumps are activated in accordance with one of a number of predetermined patterns so as to direct a particle to a destination sorting bin by directing the flow of the suspending fluid along one of a number of predetermined paths. However, the geometry of the fluid channel and the pump and valve configuration allow only a limited control over the motion of any particular cell. Moreover, the configuration does not afford simultaneous parallel control of multiple particles within the fluid. For example, the device does not contemplate directing different objects toward each other.

Particle placement and sorting are not the only tasks for which microscopic object manipulation means are desired. Many applications require the manipulation of fluids on a microscopic scale for purposes of, for example, mixing, dosing, and delivering small quantities of drug to individual cells. In other applications, objects such as strands require shape orientation or conformation. For example, in certain applications, DNA strands may need to be "unwrapped" to expose certain structural features for study. To perform these functions, complex motion of multiple particles, strand segments and surfaces is necessary. However, simultaneous arbitrary control of the trajectories of multiple objects presents a challenging controller design problem.

One device for controlling the motion of multiple objects is the Universal Planar Manipulator (UPM) developed by Dan Reznik, formerly of the University of California at Berkeley. Objects to be manipulated are placed on a rigid, horizontally oriented plate. The plate is coupled to one or more actuators which vibrates the plate in the horizontal plane. The objects are moved by means of frictional forces selectively overcome or engaged by the acceleration of the vibrating plate.

The control of motion of the objects on the UPM is achieved through a closed loop configuration consisting of a camera, for photographing the horizontal plate and the objects thereon, a set of motors for vibrating the plate and a computer for a) determining the positions of the objects at each sampling interval, b) computing the forces to be applied to each object so that the object follows its predesignated trajectory, c) computing the motion of the plate which will bring about all of the required forces, and d) applying a signal to each actuator so as to move the plate in the required manner. The process is repeated periodically according to a predetermined sampling schedule.

The UPM control method determines, at each sample period, a center of rotation (COR) about which the plate is to be rotated and the magnitude (i.e., duration) of the rotation. By strategically placing the COR at each sampling period, the required forces are generated, in a time-averaged sense, so as to move the objects in their respectively assigned trajectories.

Whereas the UPM illustrates that parallel control of multiple objects on a common medium is possible, its method of control cannot be applied to systems where gravity has much less influence on the objects than do other forces. For example, in fluidic realms, the effects of turbulence and fluid viscosity are as significant as those due to gravity. Fluid flow, in general, is a complex process presenting exceptional control challenges. Some of the unwanted effects of turbulence may be mitigated by controlling the fluid on a small size scale where the momentum of the fluid reaches negligibility. However, the control of fluid flow by acceleration (i.e., by relying on gravitational forces) on such size scales becomes highly impractical.

As shown by consideration of the shortcomings of the prior art, there is an apparent need for parallel control of multiple objects suspended or immersed in a fluid such that each object follows an arbitrary trajectory.

SUMMARY OF THE INVENTION

One aspect of the present invention provides a method for transporting objects suspended in a fluid respectively along corresponding trajectories. A microfluidic receptacle is provided to contain the fluid and the objects suspended therein. The microfluidic receptacle includes a plurality of actuators installed thereon for creating a force field within the microfluidic device. The force field respectively imparts a corresponding force on each of the objects. The microfluidic receptacle further includes a sensor for determining at least the location of each object therein. A plurality of force fields defining forces on the objects responsive to a set of actuation signals is determined for the microfluidic receptacle. The method of the present invention then determines, at each sampling interval, a destination point on a trajectory corresponding to each object. The method selects a set of force fields from the plurality of force fields for producing the forces on each object to transport it along its corresponding trajectory. A plurality of actuation signals corresponding to the set of fields is selected and respectively applied to each actuator so as to produce the total force field. Once the signals have been applied to the actuators, the method is repeated until all of the objects have traversed their corresponding trajectories.

Another aspect of the present invention provides a method for transporting a plurality of particles suspended in a fluid respectively along a corresponding one of a plurality of trajectories. A microfluidic receptacle is provided to receive the fluid in which the particles are suspended. The microfluidic receptacle includes a plurality of fluid actuators installed thereon for respectively applying a corresponding force on the fluid. A plurality of fluid flow fields defining the fluid flow responsive to a set of actuation signals is determined for the microfluidic receptacle. The method of the present invention then determines, at each sampling interval, a destination point on a trajectory corresponding to each particle. The method selects a set of fluid flow fields from the plurality of fluid flow fields for producing the fluid flow to transport each particle along its trajectory. A plurality of actuation signals corresponding to the set of fluid flow fields is selected and respectively applied to each fluid actuator so as to produce the flow. Once the signals have been applied to the fluid actuators, the method is repeated until all of the particles have traversed their corresponding trajectories.

In a further aspect of the present invention, a method is provided for sorting a plurality of particles suspended in a fluid in accordance with an attribute possessed by the particles. In this aspect of the present invention, the microfluidic receptacle includes a plurality of fluid actuators, a sensor to detect the position and attribute of each particle within the fluid, and a plurality of sorting bin locations for receiving particles having a corresponding attribute. A plurality of fluid flow fields defining the fluid flow responsive to a set of actuation signals is determined for the microfluidic receptacle. The method of the present invention then determines the attribute of each particle via the sensor at each sampling interval. The method then establishes a plurality of trajectories, one for each particle, which directs the particle to the sorting bin location receiving particles of the associated attribute. The method selects a set of fluid flow fields from the plurality of fluid flow fields that produces a fluid flow such that each particle is moved toward its corresponding sorting bin location. The method then selects the actuation signals to be applied to the actuators so that the fluid flow is produced and, once the signals have been applied, repeats the method until each of the particles has arrived at its corresponding sorting bin location.

In a further aspect of the present invention, a method is provided for conforming a strand from a first conformation to a second conformation, where the strand is suspended in a fluid. The microfluidic receptacle is provided with a plurality of fluid actuators and a sensor to detect a position of a plurality of strand segments forming the strand. A plurality of fluid flow fields defining the fluid flow responsive to a set of actuation signals is determined for the microfluidic receptacle. Once the respective position of each of the strand segments has been determined by sensor, a plurality of trajectories, one for each of the strand segments, is established and is directed to a corresponding segment position of that segment in the second conformation of the strand. The method selects a set of fluid flow fields from the plurality of fluid flow fields for that produces a flow that moves the strand segments toward the second conformation segment position. A plurality of actuation signals corresponding to the selected fluid flow fields is applied to the fluid actuators, and the method is repeated until each of the strand segments has arrived to its strand segment location in the second strand conformation.

In yet another aspect of the present invention, a method is provided for redistributing a first volume of fluid from a first distribution to a second distribution, where the first volume of fluid is immersed within a second volume of fluid and is separated therefrom by at least one fluid interface. The microfluidic receptacle is provided with the plurality of fluid actuators and a sensor to detect a position of a first plurality of segments defining the at least one fluid interface. A plurality of fluid flow fields defining the fluid flow responsive to a set of actuation signals is determined for the microfluidic receptacle. Each of the first plurality of interface segments is located via the sensor and a plurality of trajectories is established, each directed to a corresponding interface segment location defining the second distribution of fluid. A set of fluid flow fields is selected from the plurality of fluid flow fields that produces a fluid flow such that the plurality of segments is directed along its corresponding trajectory. A plurality of actuation signals corresponding to the selected fluid flow fields is applied to the plurality of fluid actuators and the method is repeated until the first plurality of interface segments has arrived at the corresponding one of the plurality of interface segments of the second distribution of the first fluid.

BRIEF DESCRIPTION OF THE DRAWINGS

FIGS. 12A-12D illustrate examples of object manipulation by the method of the present invention;

FIG. 15 is a histogram illustrating an exemplary image threshold selection method as implemented by exemplary embodiments of the present invention;

FIG. 16 is an illustration of exemplary post-threshold pixel data of an object for demonstrating run length coding image processing of exemplary embodiments of the present invention;

FIG. 17 is an illustration of object detection as implemented by exemplary embodiments of the present invention.

DESCRIPTION OF THE PREFERRED EMBODIMENTS

Prior to discussing the exemplary embodiments of the present invention, it is believed as beneficial to briefly define certain terminology as used throughout this Application for Patent. For purposes of the following, a "force field" is intended to mean a set of forces in a region of space imparting a total force vector on an object as a function of the object's position in the region of space. In this sense, force fields include, but are not limited to, electric fields in a region, magnetic fields in a region and fluid flow fields in a region.

The term "fluid" is meant to refer to non-solid media including, but not limited to, gases, liquids and gels.

The term "microfluidic" refers to properties of, and processes on, fluids constrained to regions of a physical size scale wherein inertial effects of the fluid are much less than the viscous effects thereof, i.e., a flow having a vanishingly small Reynolds number. Additionally, gravitational forces on the fluid at the physical size scale are negligible. Typically, the size scale of a microfluidic process or system is less than 1 mm.

An "object" is to be understood as an inanimate (i.e., not self-propelling) particle of arbitrary shape, an inanimate chain or strand or a region of space occupied by a fluid.

Object "conformation" is to be understood as any aspect of an object's internal or external shape or orientation. Additionally, conformation refers to an object's internal or external physical state (e.g. temperature, shear stress, etc.).

An "actuator" refers to a means for generating a force field within a region of space. This includes, but is not limited to, electrodes forming electric and magnetic fields, means for applying forces on fluids by, for example, pressure, electrical, magnetic or electromagnetic fields, thermal processes, surface tension, or electro-osmosis.

A "force field eigenmode" (or alternatively, simply "eigenmode") is a characteristic force field within a microfluidic channel or receptacle as constrained by the channel geometry, actuation type, and actuator placement.

Figure 1:
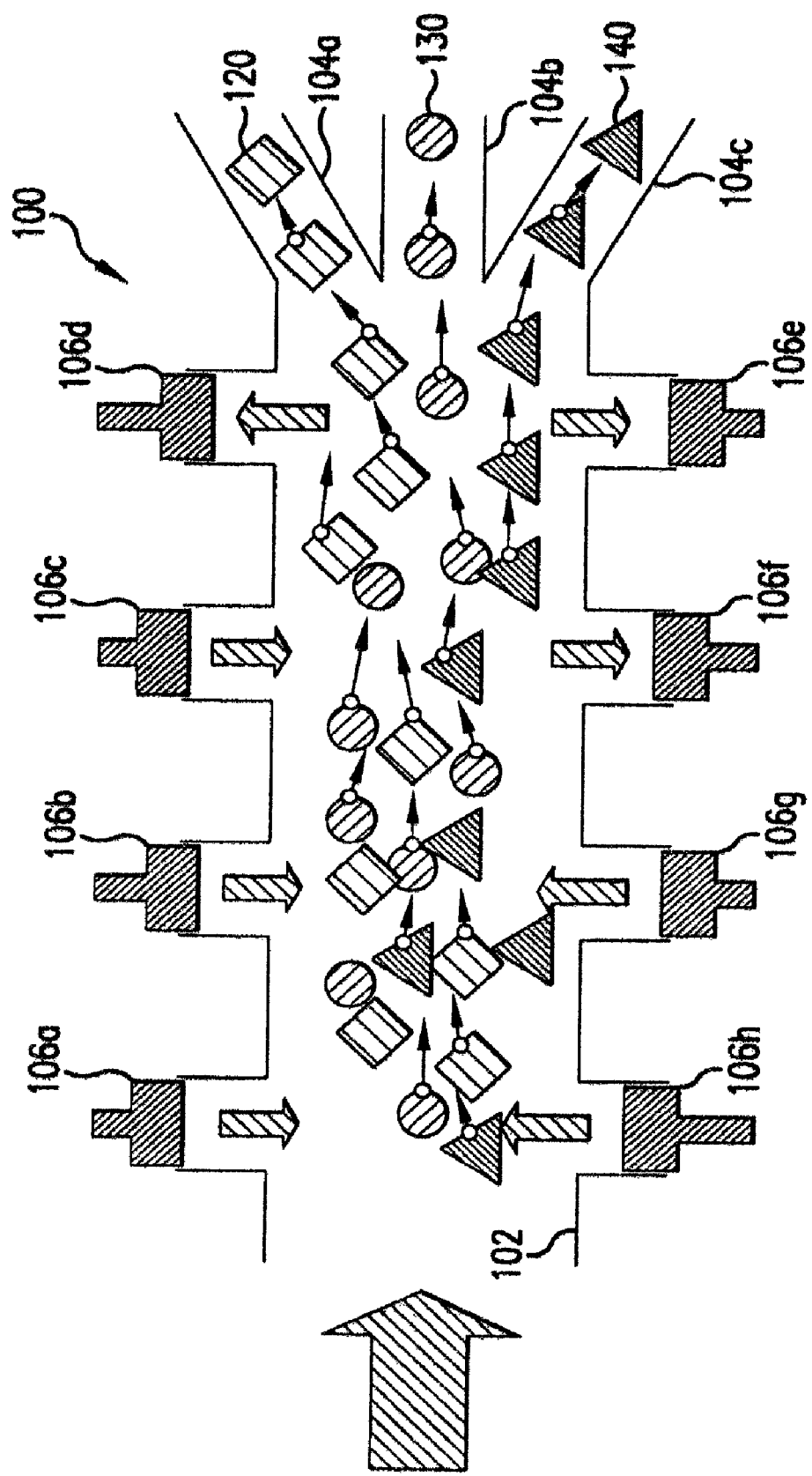
FIG. 1 is an illustration of a sorting operation as performed by an exemplary microfluidic device.

Referring now to FIG. 1, there is shown, in simplified form, an exemplary microfluidic device 100 for illustrating certain fundamental concepts of the present invention. In the embodiment of FIG. 1, microfluidic device 100 is configured to perform a sorting operation, which is a useful configuration for purposes of illustrating the basic concepts. Whereas the Figure shows the microfluidic device 100 to be of a particular shape and being fitted with actuators of a particular type, the exemplary configuration of FIG. 1 is meant to be illustrative and not restrictive. The method of the present invention is independent of a particular geometry and actuator type.

In the example of FIG. 1, a plurality of particles 120, 130, 140 having varied attributes have been introduced into channel 102 by means of a suspending fluid. The objective of the sorting operation is to transport particles 120 to sorting bin location 104a, particles 130 to sorting bin location 104b, and particles 140 to sorting bin location 104c. Whereas, the sorting bin locations 104a-104c are shown in FIG. 1 as physically separated ports, the sorting bins may also be simply a separated region of microfluidic device 100 in which particles of a certain type are congregated.

At periodic time intervals, i.e., once every sampling period, the positions of each of the particles within the fluid channel 102 are sensed by a particle position sensor, such as by exemplary methods discussed in paragraphs that follow. From each of these particle locations, a local particle trajectory is computed to set each particle on a path towards its corresponding sorting bin location 104a-104c. By means of the present invention, it is then determined what local force field vector would cause a corresponding force on the particle so that the particle is conducted along its corresponding trajectory. The force may be, for example, an electric or magnetic field or may be a flow vector of the fluid in contact with the object. For purposes of description, the latter of the fields is assumed.

As is shown in the Figure, microfluidic device 100 is adapted to receive a plurality of actuators 106a-106h. The actuators 106a-106h are independently operated to produce a local fluid current flow about its corresponding location. It is an object of the present invention to respectively apply an appropriate signal to each actuator 106a-106h to produce an underlying current flow of the fluid suspending particles 120, 130, 140 so that the force applied to each particle is approximately equal to the force required to transport that particular particle along its corresponding trajectory.

It should be clear from the simplified diagram of FIG. 1 that control of the suspending fluid defines the controllability of each of the suspended particles. In a microfluidic channel, the size of the microchannel 102 minimizes the effects of inertia of the fluid. Thus, a cross-channel flow as created by one of actuators 106a-106h will not be sustained beyond the time the actuator is applying a force to the fluid. Turbulent flows are thereby minimized and the particle follows the trajectory as influenced by the fluid flow in an approximately linear fashion.

By way of example, the system of FIG. 1 illustrates an object of the present invention, namely the control of objects held within a microfluidic system. As previously stated, the objects are controlled by forces exerted thereon through the force field, which, in the example of FIG. 1 is through the flow of the surrounding fluid as created by the fluid actuation mechanism. The method of the present invention may be used on a wide variety of microfluidic devices implementing a wide variety of actuation mechanisms.

The present invention provides a method by which multiple objects within a microfluidic receptacle may be respectively transported along corresponding trajectories. A microfluidic receptacle of a given geometry and having a given actuation mechanism (e.g., a complex electric field generated by a plurality of electrodes or a complex fluid flow generated by pumps or other means described below) is capable of supporting a set of force fields therein. As will be shown in paragraphs that follow, selecting a subset of supported force fields provides stable, parallel control of the motion of the objects within the microfluidic receptacle.

To implement the present invention, a model of the forces on the objects contained within a microfluidic system provides insight as to hoe the force fields supported by the device may be used in the control method of the present invention. Once the supported force fields have been ascertained, they may be subsequently selected and combined to control the motion of the objects. An exemplary embodiment of the present invention is now presented in a microfluidic system implementing an electro-osmotic actuation mechanism.

The fluid flow in any microfluidic system having a minimum device length well above the mean free path of the molecules composing the fluid can be accurately modeled by the Navier-Stokes equations:

$$\nabla \cdot v^* = 0 \qquad (1)$$

$$\rho\left(\frac{\partial v^*}{\partial t^*} + v^* \cdot \nabla v^*\right) = -\nabla P + \eta^* \nabla^2 v^* \qquad (2)$$

where $v^*$ is the fluid velocity field, $\rho^*$ is the density, $P^*$ is the pressure, $\eta^*$ is the viscosity. Here the asterisk denotes dimensional quantities.

For the microfluidic devices of interest, inertial effects are negligible compared to the effects of viscosity and Equation (2) may then be reduced to:

$$\frac{\partial v^*}{\partial t} = -\frac{1}{\rho}(\nabla P^* - \eta \nabla^2 v^*) \qquad (3)$$

It is thus apparent from Equation (3) that a change in the fluid flow field may be brought about by either a gradient in the pressure of the fluid or by viscous coupling to a moving object (since inertia is minimal at these scales). It is the choice of actuation and a corresponding choice in microfluidic channel geometry that defines the controllability of the fluid flow. Equation (3) may thus be used to derive a set of control equations once the geometry and actuation mechanism for a particular microfluidic application have been chosen.

Figure 2A:
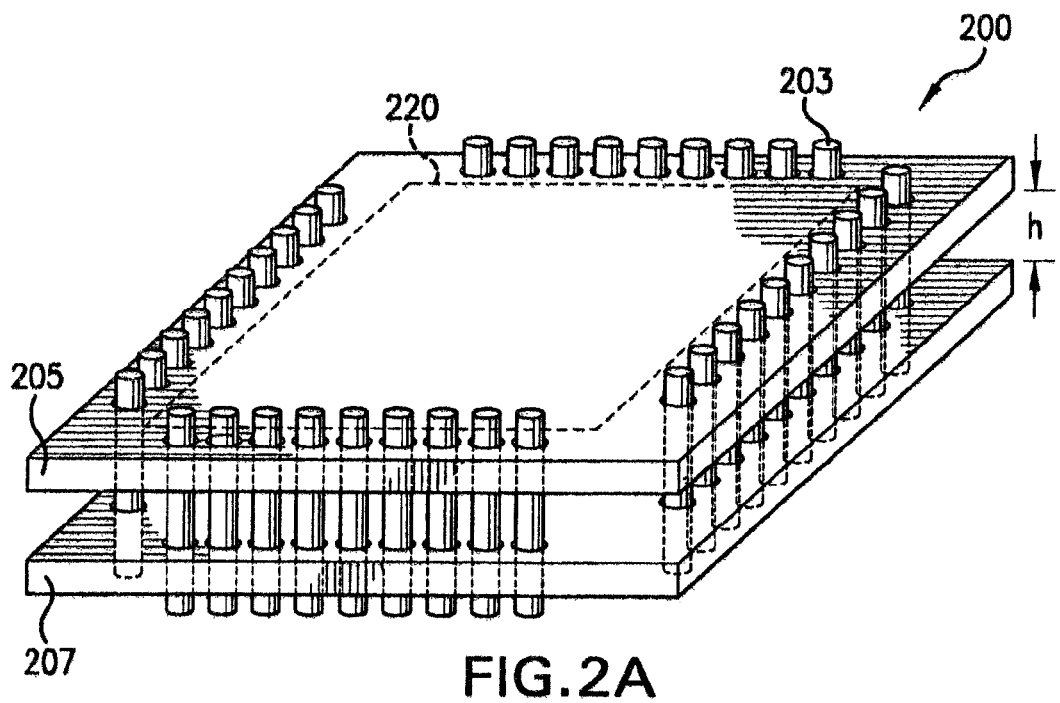
FIG. 2A is an illustration of the construction of an exemplary electro-osmotic microfluidic device.
Figure 2B:
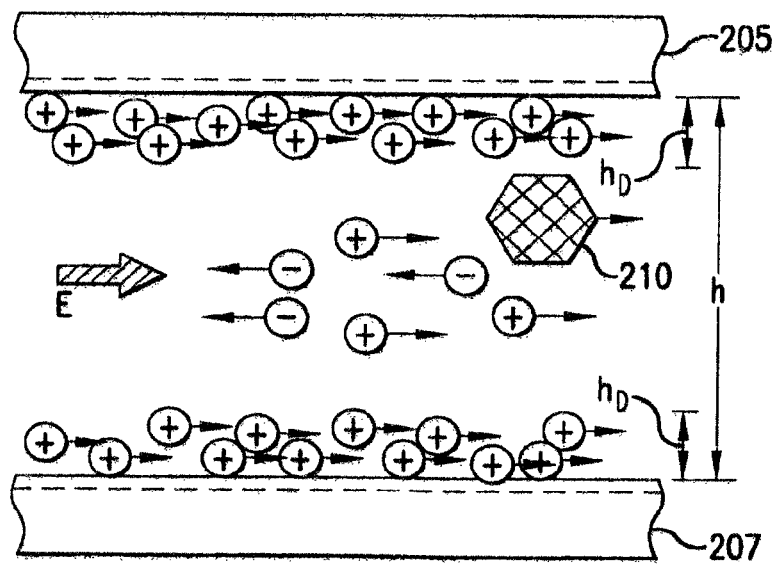
FIG. 2B is a cross-sectional view and functional illustration of the electro-osmotic device of FIG. 2A.

An exemplary embodiment of the electro-osmotic microfluidic device is illustrated in FIGS. 2A-2B. The microfluidic device 200 is constructed from a pair of parallel, non-conducting plates 205, 207 separated by a distance h. Passing through both plates and simultaneously isolated therefrom is a plurality of electrodes 203, which, as will be shown below, provides an electrically motivated viscous coupling to the fluid which serves as the exemplary actuating mechanism.

When an aqueous (polar) fluid, such as water, is introduced to the microfluidic chamber 220, an electrical double layer of ions, commonly referred to as the Debye layer, is formed at the plate/liquid interface as is shown in FIG. 2B. The Debye layer is caused by such mechanisms as ionization, ion adsorption, and ion dissolution. The plurality of the charge depends on the material used for manufacturing the plates. When an electric field, E, is applied along the chamber, i.e., parallel to the plate surface, the Debye layer is displaced. The displaced Debye layer moves in accordance with the electric field and the fluid adjacent to the charge layer is "dragged" thereby through viscous coupling. This is the process commonly referred to as electro-osmotic flow. Note that any free floating ions within the fluid contribute a small amount to the motion of the fluid, such motion being a system noise component which may be overcome by control techniques, as will be discussed below. Moreover, the particles contribute to Brownian noise of the motion of an object, which places a lower bound on the size of the target object (i.e. the smaller the object, the greater is the degree to which Brownian noise influences the motion of the object). The Brownian noise is may also be overcome by control techniques such as those described below.

When a small object 210 is placed in the microfluidic chamber 220 of microfluidic device 200, the trajectory thereof follows the local fluid flow of the suspended fluid. Thus, as will be detailed in paragraphs that follow, the trajectory of object 210 may be controlled by selective application of an electric potential on one or more of the plurality of electrodes 203. The electric field produces a corresponding fluid velocity field serving as the exemplary force field.

The Debye layer thickness; $h_D$, (10 nm in most cases) is very small compared to the chamber dimensions (1 cm×1 cm×0.05 mm in the exemplary device), the boundary conditions at the walls are accurately captured by the velocity slip conditions, $$v^*_{wall}(x^*, y^*, z^* = \pm h^*/2) = \frac{\varepsilon^* \xi^*}{\eta^*} \nabla \Phi^*(x^*, y^*) \quad (4)$$

where $\in^*$ is the permittivity of the fluid $\xi^*$ and is the zeta potential at the wall. The electric potential $\Phi^*$ satisfies the Laplace equation $$\nabla(\in^* \nabla \Phi^*) = 0 \quad (5)$$

with the boundary conditions of the applied voltage at the $i^{th}$ control electrode given by $$\Phi^*(\partial D_i) = u^*_i \quad (6)$$

where $u^*_i$ is the electric potential of the $i^{th}$ electrode, and $\partial D_i$ denotes the electrode surface.

If the viscosity and surface properties are uniform and the fluid velocity at the inlets is given by (7):

$$v^*_{inlet} = \frac{\varepsilon^* \xi^*}{\eta^*} \nabla \Phi^*_{inlet} \quad (7)$$

then the quasi-steady state solution to partial differential equations (1) and (2) is simply given by $$v^*(x^*, y^*, z^*) = -\frac{\varepsilon^* \xi^*}{\eta^*} \nabla \Phi^*(x^*, y^*)_{z^*} \quad (8)$$

showing that the velocity profile is uniform in the vertical z direction (perpendicular to plates 205 and 207). Though the condition (7) is not satisfied at the surface of the electrodes (at the electrode surface the velocity should vanish to zero due to no-slip boundary conditions), the flow field relaxes to satisfy this condition within a few lengths of the channel height from the electrode surfaces and so (8) can be used to predict the fluid velocity in the domain except very near to the electrode surfaces.

The condition on how slowly the electrode voltages can be varied for the fluid flow to maintain a quasi-steady state should be determined to ensure controllability. The time required for the fluid flow in the exemplary device filled with water ($\rho^*$=1000 kg/m³, $v^*$=1 mm/s,$h^*$=0.05 mm, $\eta^*$=0.001 Ns/m²) to reach the steady state of (8) in response to a step voltage input has been determined to be on the order of 1 μs. Thus, if the electric field is varied such that the time period of the highest frequency input voltage is much greater than 1 μs, the velocity of the fluid at all times may be given by (8).

The motion of an object within the fluid follows the motion of the fluid local to the object. Thus, at any time t, the velocity of the $j^{th}$ object at position $p_j^*=(x^*_j, y^*_j)$ is given by $$\frac{d}{dt} p_j^* = v^*(p_j^*) = \nabla \Phi^*(p_j^*) \quad (9)$$

For convenience, the dimensionalized equations above may be non-dimensionalized as follows. Since the numerical values of $x^*, y^*, |p^*_j|$ are of the order of $L^*$; and $\Phi^*, u^*$ are of the order of $|u^*_{max}|$ and $|v^*_{max}|$ is of the order of $|v^*_{max}|$, the relations $$\Phi = \frac{\Phi^*}{u^*_{max}}, \quad v = \frac{v^*}{|v_{max}|}, \quad (10)$$

$$x = \frac{x^*}{L^*}, \quad y = \frac{y^*}{L^*}, \quad z = \frac{z^*}{h^*}$$

$$p_j = \frac{p_j^*}{L^*}, \quad u_i = \frac{u_i^*}{u^*_{max}}$$

$$|v_{max}| = \frac{\varepsilon^* \xi^*}{\eta^*} \nabla \Phi^* = \frac{\varepsilon^* \xi^* u^*_{max}}{\eta^* L^*}$$

can be used to write the equations of the system in dimensionless variables as $$\nabla^2 \Phi = 0 \quad (11)$$

$$v = \nabla \Phi \quad (12)$$

$$\dot{p}_j = v(p_j) \quad (13)$$

with boundary conditions $$\Phi(\partial D_i) = u_i \quad (14)$$

Figure 3:
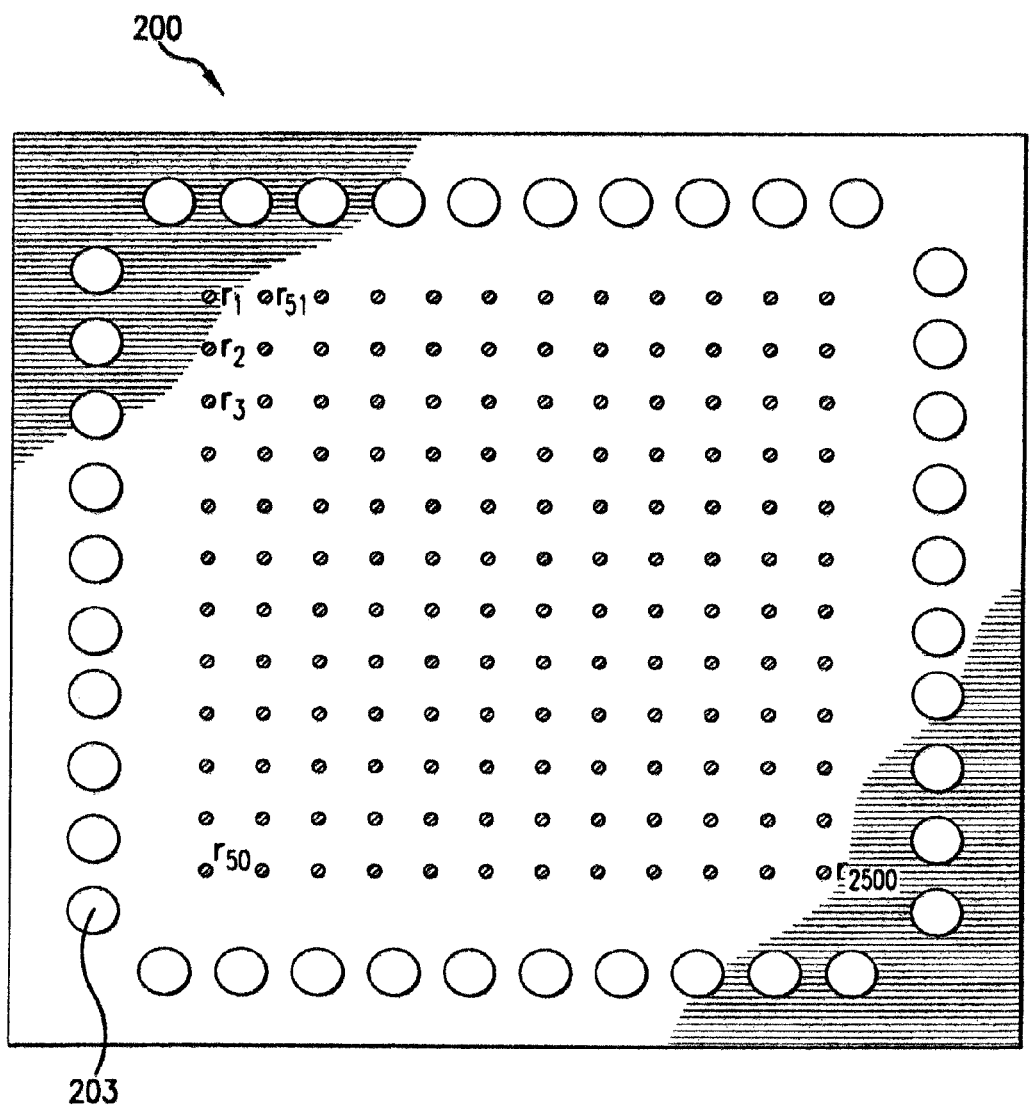
FIG. 3 is an illustration of an exemplary discrete sample space of the microfluidic chamber of the electro-osmotic device.
Figure 4:
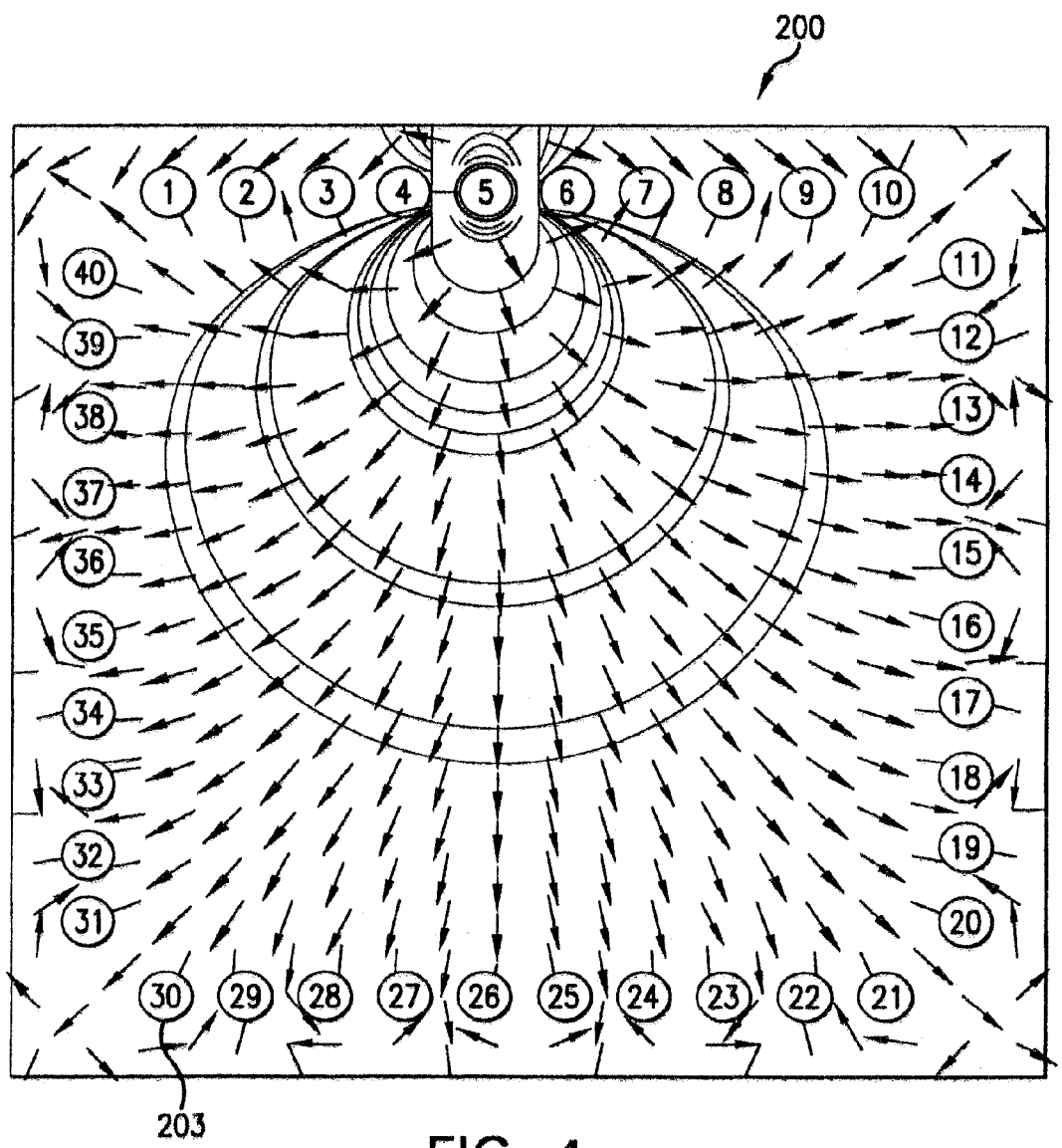
FIG. 4 is an illustration of a fluid flow field for the exemplary electro-osmotic device.

The non-dimensionalized system of equations (11), (12), and (14) are linear and contain no time derivatives, so at any time t the velocity field v can be expressed as a superposition of velocity fields $\nabla \Phi_i (1, 2, \ldots, n)$ as follows $$v(x, y; u) = \nabla \Phi(x, y; u) = \sum_{i=1}^{n} u_i \nabla \Phi_i(x, y) \quad (15)$$

where $\Phi_i$ solves $$\nabla^2 \Phi_i = 0 \quad (16)$$

with boundary conditions $$\Phi(\partial D_i) = 1, \Phi(\partial D_j) = 0, j \neq i \quad (17)$$

where n is the number of electrodes and $u = [u_1 \ u_2 \ \ldots \ u_n]$ represents the vector of electrode voltages. An exemplary velocity field $\nabla \Phi$ is shown in FIG. 3.

Now, since u and u−c (c being some arbitrary constant) generate the same velocity field v, a vector u may always be chosen such that a particular electrode voltage is always 0. In other words any achievable velocity field can be expressed as a linear superposition of any n−1 fields out of $\nabla \Phi_i$ (i=1, 2, ..., n) which constitute a linearly independent set. Hence we can rewrite (15) as $$v(x, y; u) = \nabla \Phi(x, y; u) = \sum_{i=1}^{n-1} u_i \nabla \Phi_i(x, y) \quad (18)$$

If at time t, the objects are at positions $p_1=(x_1, y_1), p_2=(x_2, y_2), \ldots, p_m=(x_m, y_m)$, then the velocity of the $j^{th}$ object is given by $$p_j = v(p_j) = \nabla\Phi(p_j) = \sum_{i=1}^{n} u_i \nabla\Phi_i(p_j) = A(p_j)\cdot u \quad (19)$$

Let $v_{1D}, v_{2D}, \ldots, v_{mD}$ be the desired object velocities at time t. It is desired to proportionally combine the velocity fields $\nabla\Phi_i$ so that the fluid velocities at $p_1, p_2, \ldots, p_m$ are as close to $v_{1D}, v_{2D}, \ldots v_{mD}$ as possible. Such a voltage vector $u_{opt}$ can be obtained by solving the least squares problem mint $$\min\|v_D - A\cdot u_{opt}\|_2 \quad (20)$$

where $$v_D = [v_{1D}\ v_{2D}\ \ldots\ v_{mD}]^T \quad (21)$$

$$u_{opt} = [u_{1opt}\ u_{2opt}\ \ldots\ u_{nopt}]^T \text{ and}$$

$$A[p] = \begin{bmatrix} \nabla\Phi_1(p_1) & \nabla\Phi_2(p_2) & \ldots & \nabla\Phi_n(p_1) \\ \nabla\Phi_1(p_2) & \vdots & \ldots & \vdots \\ \vdots & \vdots & \ddots & \vdots \\ \nabla\Phi_1(p_m) & \nabla\Phi_2(p_m) & \ldots & \nabla\Phi_n(p_m) \end{bmatrix}$$

the analytical solution of which is given by $$u_{opt} = [A^T(p)A(p)]^{-1}A(p)v_D. \quad (22)$$

When 2m is less than n−1 (i.e., when the twice the number of objects is less than one less than the number of actuators), Equation (22) constitutes an underdetermined system of linear equations which has multiple solutions. The least square optimal solution is that with the smallest norm which allows the required velocities to be reached with minimal applied voltage. Ideally, the optimal solution generates the required velocity field by combining the lowest order eigenmodes of the available force field eigenmodes. The higher eigenmodes require large voltage components in the solution $u_{opt}$ while having an insignificant impact on $v_D$. As a result, small changes in $v_D$ introduces large changes in $u_{opt}$. This instability imposes significant obstacles in the control of the fluid and thereby the motion of the objects suspended therein.

Increasing the number of objects imposes other restrictions on the velocity field, i.e., higher eigenmodes of the velocity field must be evoked. Thus, attempting to overcome the control deficiencies by adding actuators to the system fails to do so. To stabilize the system, only a subset of the force field eigenmodes are implemented in the control method, by way of the present invention, as will now be discussed.

Methods for suppressing the higher eigenmodes and to stabilize the least squares solution are widely known. For example, Tikhonov regularization works by solving the modified problem, $$\min\{\|v_D - A(p)u_{opt}\|_2^2 + \lambda^2\|u_{opt}\|_2^2\} \quad (23)$$

Another optimization method is TSVD (truncated singular value decomposition), which as the name suggests, works by expressing the solution space as a superposition of only a finite number the lower eigenmodes and discarding the higher eigenmodes of the system. In certain embodiments of the present invention, TSVD is utilized to select the set of implemented force field eigenmodes. From the solution of Equation (15), $$v(x, y; u) = \sum_{i=1}^{n} u_i \nabla\Phi_i(x, y) \quad (24)$$

on a set of discrete q×q rectangular grid points $r_i$ in the domain, where q is chosen such that the grid may resolve the fluid velocity field sufficiently. Thus, $$v(r_i) = D(r)u\ i = 1, 2, \ldots q^2 \quad (25)$$

where, $$D(r) = \begin{bmatrix} \nabla\Phi_1(r_1) & \ldots & \nabla\Phi_n(r_1) \\ \nabla\Phi_1(r_2) & \ldots & \vdots \\ \vdots & \vdots & \vdots \\ \vdots & \vdots & \vdots \\ \nabla\Phi_1(r_{q^2}) & \vdots & \nabla\Phi_n(r_{q^2}) \end{bmatrix} \quad (26)$$

$$v = \begin{bmatrix} v(r_1) \\ v(r_2) \\ \vdots \\ \vdots \\ v(r_{q^2}) \end{bmatrix},\ u = \begin{bmatrix} u_1 \\ \vdots \\ u_n \end{bmatrix}$$

where $r_i$ denotes the position vector of the $i^{th}$ grid point as shown in FIG. 3 (q=50). Note that the matrix $D(r)$ is the discrete-space representation of the matrix $A(p)$. The matrix D is then decomposed using singular value decomposition so that $$D = M \times \Omega \times N^T$$

where $$M = [M_1\ M_2\ \ldots\ M_n] \quad (27)$$

$$\Omega = \begin{bmatrix} \sigma_{11} & 0 & 0 & 0 \\ 0 & \sigma_{22} & 0 & 0 \\ 0 & 0 & \ddots & 0 \\ 0 & 0 & 0 & \sigma_{nn} \\ 0 & 0 & 0 & 0 \\ 0 & 0 & 0 & 0 \end{bmatrix}$$

$$N = [N_1\ N_2\ \ldots\ N_m].$$

The $i^{th}$ force field (fluid flow) eigenmode is then given by $$Ei = \sum_{j=1}^{n} N_{ji} \nabla\Phi_j(x, y)$$

The TSVD forces the column vectors M and N to satisfy:

$$\|M_i\|^2 = 1 \text{ and } \|N_i\|_2 = 1 \quad (28)$$

Figure 5A:
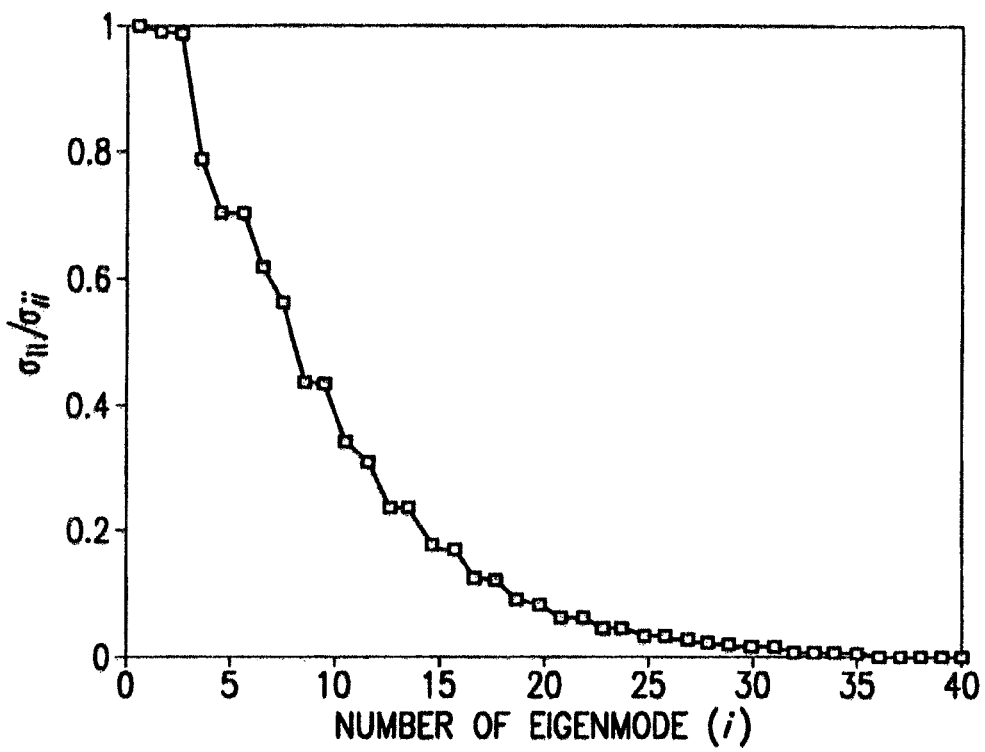
FIGS. 5A-5B are graphs of relative strengths of a given eigenmode to the first eigenmode of the exemplary electro-osmotic device.

Thus, the application of unit voltage vector $N_i$ produces a unit velocity field vector n amplified by $\sigma_{ii}$. The ratio $\sigma_{11}/\sigma_{ii}$ indicates the strength of the first mode of the velocity field in comparison to the $i^{th}$ mode when a voltage vector of identical strength is applied to the corresponding electrodes of the exemplary device in both cases. This ratio is illustrated in FIG. 5A, which shows that the effect of higher order modes do not influence the flow field as much as the lower order modes. As such, only a limited number of eigenmodes need be implemented.

As previously discussed, the control of the motion of objects within the microfluidic device is stabilized by selecting a subset of possible eigenmodes for implementation. If the subset of is chosen as k eigenmodes, k≦m, a new matrix, Ñ can be constructed from the first k columns of N. Then, a new matrix, Ã, may be formed from the original matrix A such that, $$\tilde{A}(p) = A(p)\tilde{N}[\tilde{N}^T\tilde{N}]^{-1}\tilde{N}^T, \quad (29)$$

and, then, $$\dot{p} = \tilde{A}(p) \cdot u \quad (30)$$

The actuator signals for the stabilized control method is then given by, $$u_D = [\tilde{A}^T(p)\tilde{A}(p)]^{-1}\tilde{A}(p)v_D \quad (31)$$

where $u_D$ is the stabilized actuator input corresponding to the desired force field, $v_D$.

Figure 5B:
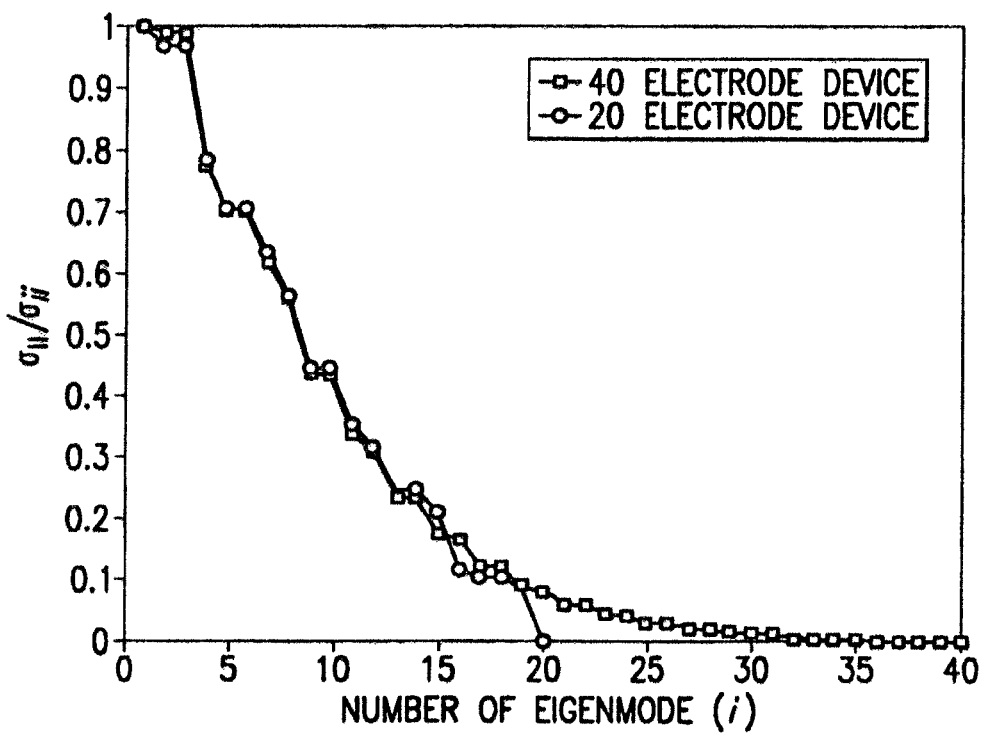

A further design consideration lies in the number of actuators to implement. As previously stated, only the lower order fluid flow eigenmodes contribute significantly to the fluid flow. As such, a smaller number of actuators (electrodes in the exemplary device) need be installed. This is shown in the graph of FIG. 5B, where the ratio $\sigma_{11}/\sigma_{ii}$ is shown for both a 40 electrode device and a 20 electrode device. Thus, in certain embodiments of the present invention where the number of objects being controlled is less than number of eigenmodes required to control those objects, the number of actuators may be decreased accordingly.

Figure 6A:
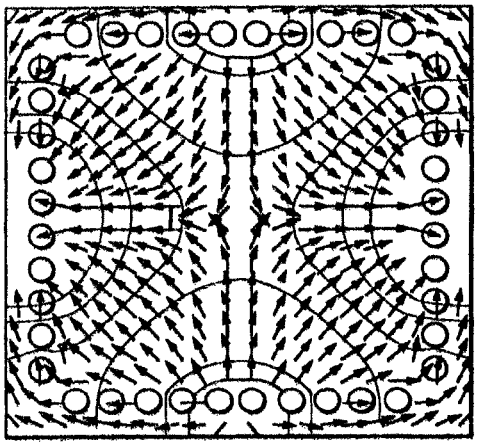
FIGS. 6A-6F illustrate various fluid flow fields of the exemplary electro-osmotic device.
Figure 6B:
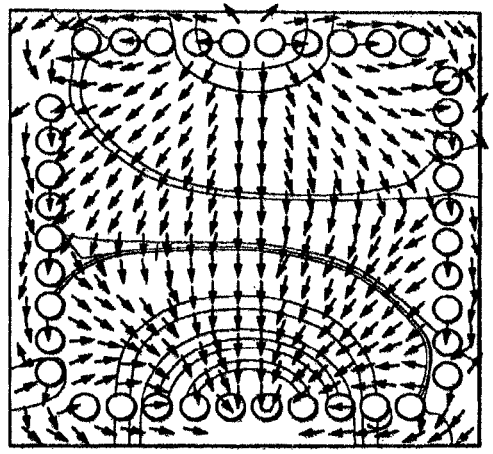
Figure 6C:
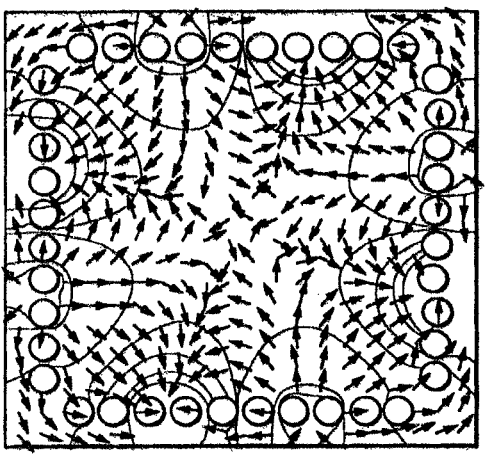
Figure 6D:
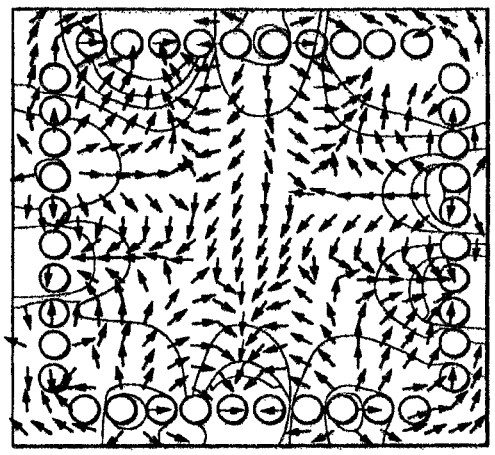
Figure 6E:
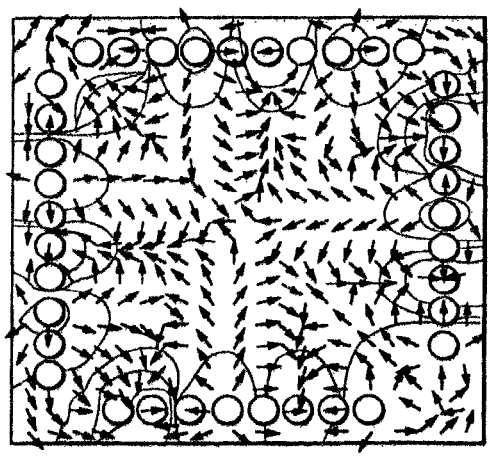
Figure 6F:
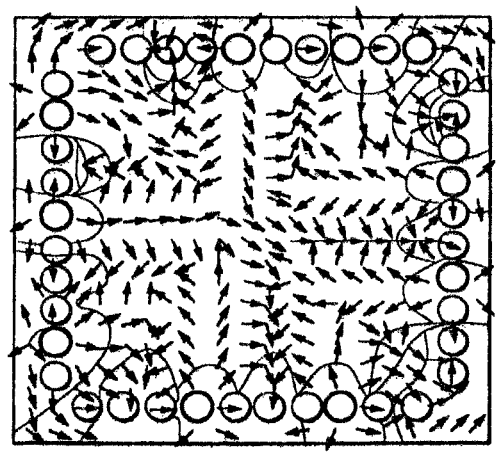

FIGS. 6A-6F illustrate the fluid flow in accordance with a corresponding eigenmode. FIG. 6A illustrates eigenmode 1 (i=1), FIG. 6B illustrates eigenmode 3 (i=3), FIG. 6C illustrates eigenmode 7 (i=7), FIG. 6D illustrates eigenmode 10 (i=10), FIG. 6E illustrates eigenmode 14 (i=14), and FIG. 6F illustrates eigenmode 18 (i=18). It should be clear from these Figures how a prudent combination of fluid flow eigenmodes influences the local fluid flow and, thereby, the objects suspended therein.

Having now described an exemplary microfluidic device, a system for implementing the method of the present invention is described with reference to FIG. 7. As is illustrated in the Figure, microfluidic device 200 includes a plurality of actuators 203a-203d. Microfluidic device 200 is of an appropriate geometry and is fitted with the appropriate actuation mechanism for carrying out a variety of object control tasks such as the electro-osmotic device previously described.

Microfluidic device 200 is coupled to sensor 730 by which the positions of objects within the microfluidic device are located and the attributes of the objects may be ascertained. The present invention may be implemented by any object sensor means capable of locating the objects to within a desired accuracy. Such sensor means includes, but is not limited to, microscopic cameras, fiber optics, electromagnetic sensors and thermal sensors. The sensor should, of course, be appropriate to determine the property of the object upon which control thereof is conditioned.

Coupling of the sensor 730 to microfluidic device 200 need not be a physical connection (as indicated by the dashed line). For example, sensor 730 may be a digital camera fitted with optics appropriate to view the objects in microfluidic device 200. In certain embodiments of the present invention, the optics may be part of a microscope, the camera being coupled to the ocular part thereof. In such embodiments, it should be apparent that one or more of the plates 205, 207 of microfluidic device 200 be transparent to provide optical access to the objects in the microfluidic chamber 220. Images captured by the camera may be processed by known image processing techniques to determine an object's position, conformation, or other attribute, an exemplary embodiment of which will be described in paragraphs below.

Actuators 203a-203d are respectively coupled to an amplifier or transducer of amplifier/transducer stage 720. Amplifier/transducer section 720 converts electrical signals from computer 710, into signals appropriate to the actuator type. For example, if actuators 203a-203d are driven by the pressure of a gas, amplifier/transducer section 720 controls the gas pressure for each actuator responsive to an electrical signal supplied by computer 710. In other embodiments, such as the electro-osmotic device described hereinabove, amplifier/transducer section 720 conditions the electrical signal from computer 710 to an electrical signal having an electric potential appropriate to the corresponding actuator.

Figure 7:
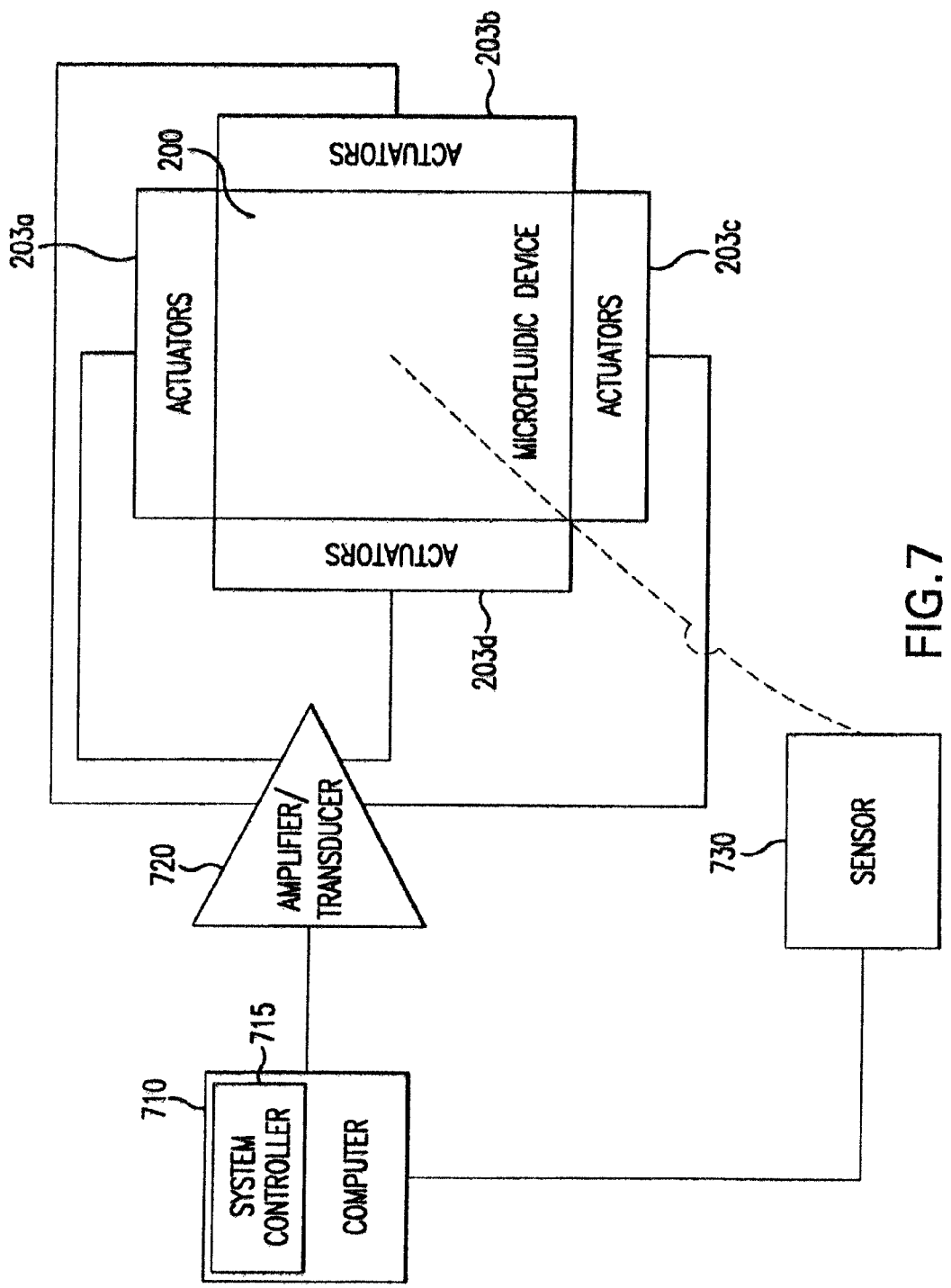
FIG. 7 is a block diagram of an exemplary system on which the method of the present invention may be deployed.

Computer 710 is configured as the controller of the system of FIG. 7. The computer 710 receives images from a sensor 730, processes those images to determine the appropriate properties of the objects of interest in the microfluidic device 200, determines the correct trajectory for each of the objects in accordance with the method of the present invention, and produces an output signal to amplifier/transducer section 720 so as to produce the current flow required to move the objects along the corresponding trajectory. Note that whereas the system of FIG. 7 is illustrated as a system of discrete components, the system may be constructed as a single, self-contained unit.

As is illustrated in FIG. 7, computer 710 forms the operational platform for a system controller 715. It should be clear, however, that computer 710 may perform other functions, such as providing a user interface to the system, and such functions may be implemented by numerous methods well-known in the art. Thus, only the details of system controller 715 will be described further.

In certain embodiments of the present invention, system controller 715 is implemented as a Time Varying Linear Quadratic Regulator (TVLQR) such as is well-known in the optimal control art. The TVLQR may be adapted to compensate for errors in position of the objects being controlled by system controller 715.

As was developed in paragraphs hereinabove, the desired position of an object $p_D(t+\Delta t)$ is set by an input to the actuators by the relationship $$p_D(t+\Delta t) = A[p_D(t+\Delta t)]u(t+\Delta t) \quad (32)$$

As is the case with any physical system, there will be errors in the object's position after the actuation cycle has been completed. This positional error, denoted hereinafter as $p_E(t)$, results from shortcomings of the model to accurately portray the physical process of the fluid flow within the microfluidic device, deviations from nominal in the actual actuator signals, movement of the object through Brownian motion, as well as other system noise sources.

If the position of the object is represented as a sum of the desired position and the positional error, i.e., $$p_T(t) = p_D(t) + p_E(t), \quad (33)$$

then the position of the object at some future time $t+\Delta t$ is given by $$\dot{p}_T(t) = p_D(t) + p_E(t) + A[p_D(t+\Delta t) + p_E(t+\Delta t)][u_D(t+\Delta t) + u_E(t+\Delta t)] \quad (34)$$

where, $$\dot{p}_T(t) = p_T(t+\Delta t). \quad (35)$$

The vector $u_E(t)$ represents the actuation signal that would bring about the positional error $p_E(t)$.

In a manner consistent with optimal control theory, the positional error of the objects under control of system controller 715 may be modeled by $$\dot{p}_E(t) = F(t)p_E(t) + G(t)u_E(t) \tag{36}$$

where F(t) and G(t) contain the coefficients to the differential equation characterizing the error behavior of the open loop system. Using this model for the positional error, $\dot{p}_E(t)$, it is desired to correct the positional deviation from an initial non-zero state $p_E(t_o)$ to a final state $p_E(t_f)=0$, where $t_f$ is the time within which the positional error is to be extinguished. The corrective actuation signal, $u_E(t)$ can be found by minimizing the cost function $$J = \int_0^{t_f} [p_E^T(t)Q(t)p_E(t) + u_E^T(t)R(t)u_E(t)]dt \tag{37}$$

where Q(t) and R(t) are positive definite matrices and are chosen to insure realizability of $u_E(t)$ and $p_E(t)$. The actuation signal that solves this optimization problem is known to be, $$u_E(t+\Delta t) = -K(t)p_E(t) \tag{38}$$

where, $$K(t) = Q^{-1}(t)G(t)S(t) \tag{39}$$

The matrix S(t) is the solution to the Ricatti differential equation, $$\dot{S}(t) = -S(t)F(t) - F^T(t)S(t) + S(t)G(t)R^{-1}(t)G^T(t)S(t) - Q(t) \tag{40}$$

$$S(t_f) = 0, \tag{41}$$

where $$\dot{S}(t) = S(t+\Delta t) \tag{42}$$

Figure 8:
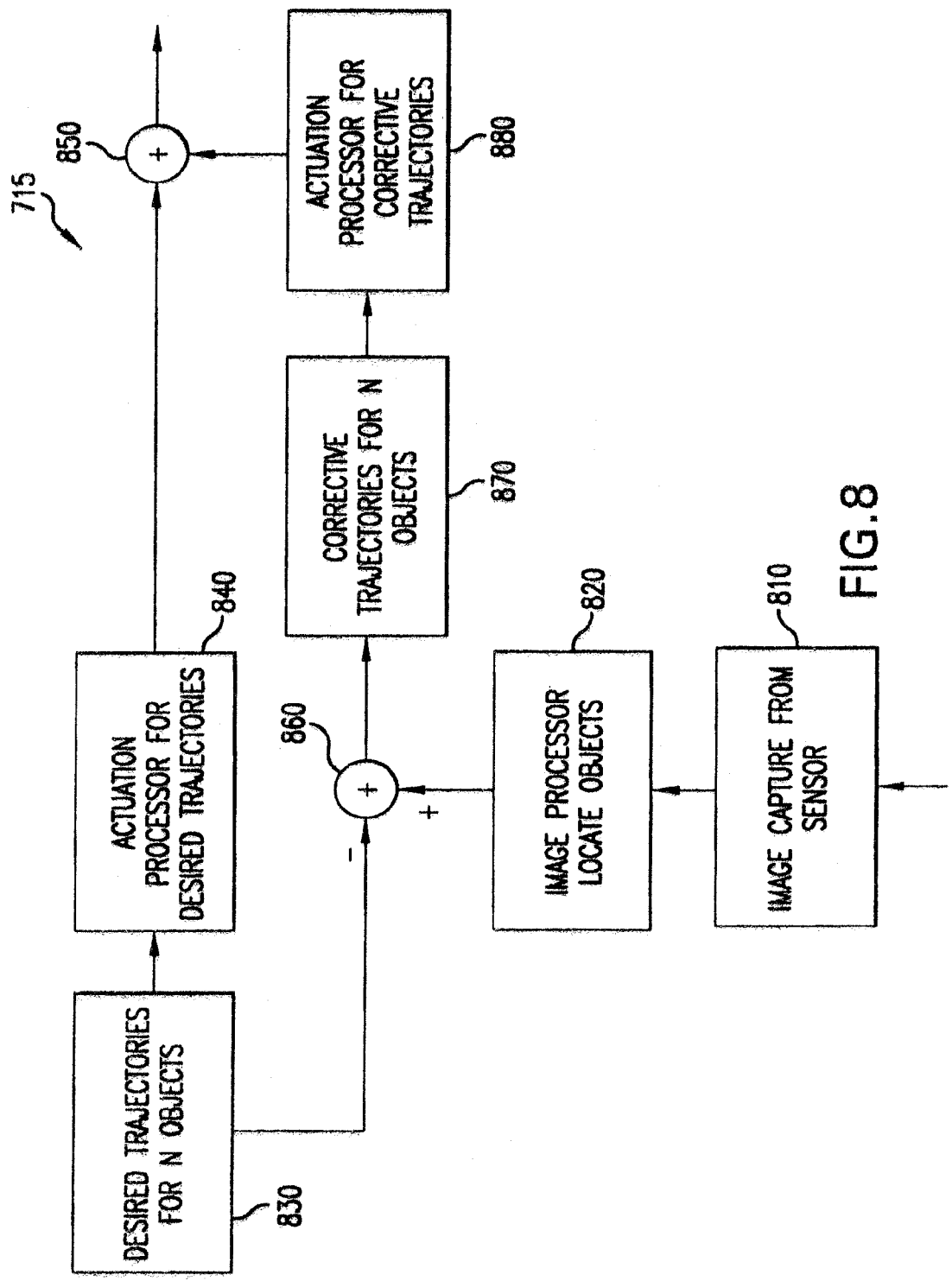
FIG. 8 is a block diagram of exemplary functional components for executing the method of the present invention.

A block diagram of an exemplary set of processing functions of computer 710 is depicted in FIG. 8. The processing functions may be distributed across multiple computing platforms or may be performed on a single computing device. It should be clear to the skilled artisan that such distribution of functions is intended to fall within the scope of the present invention.

As shown at block 830 of FIG. 8, the desired trajectories for N objects contained within the microfluidic chamber 220 are computed. The trajectories may be computed a priori and held within a table in memory or may be computed dynamically as, for example, by user input to the system. In certain embodiments of the present invention, the trajectories are maintained as a series of object positions at which the N objects are to be located at a given time period.

The desired trajectories are provided to actuation processor 840, which determines the force field required to transport the N objects along their respective trajectories. Actuation processor 840 provides at its output a vector of actuation signals that, when applied to the actuation system of the microfluidic device, produces the computed force field.

At prescribed sampling intervals, an image of the microfluidic chamber 220 is acquired via sensor 730 as shown at block 810. In certain embodiments of the present invention, the image data are in the form of pixels, each having a value corresponding to physical properties of the fluid and objects suspended therein at the corresponding pixel location. For example, in the case where the image is constructed of optical data, the value of each pixel may correspond to optical transmissivity of the fluid (and objects suspended therein) at the location in the microfluidic chamber 220 corresponding to the pixel location.

The captured image is transferred to image processor 820 by which the N objects are located and characterized. Any known image processing technique capable of isolating multiple objects of varying conformation, density, distribution, etc. may be utilized by the present invention and an exemplary embodiment will be described with reference to FIGS. 14-18. The results of the image processing function 820 should be the location and characteristics of the N objects identified and corresponding to the N objects of block 830.

The actual object locations as determined by the image processor 820 are compared with the desired trajectories computed at block 830 at summing node 860, the output of which is a positional error for each of the N objects within the microfluidic chamber 220. The positional error for each object is used to compute a corresponding corrective trajectory at block 870. The corrective trajectory is one which is directed from the actual location of the corresponding object to its desired position. The corrective trajectories are provided to eigenmode processor 880 which determines the underlying fluid flow to move each object along its corrective trajectory and provides at its output the corresponding actuation signals. The actuation signals of eigenmode processor 840 and those of eigenmode processor 880 are combined at summing node 850 to produce a set of total actuation signals which are subsequently applied to the actuators of the microfluidic device.

Figure 9:
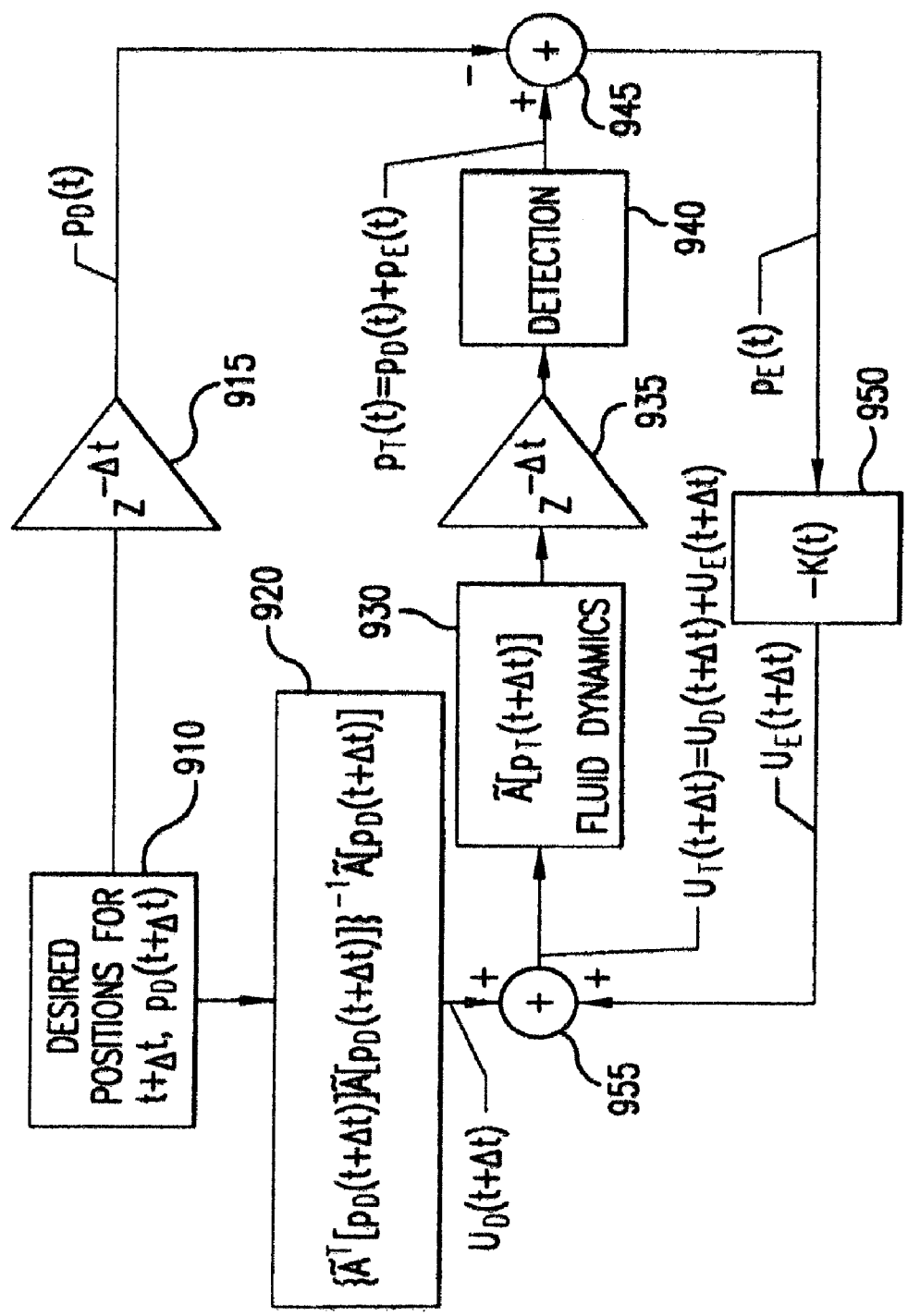
FIG. 9 is a control diagram of an exemplary embodiment of the present invention.

Referring now to FIG. 9, there is shown a control diagram of an exemplary TVLQR of the present invention. A vector containing the positions at time t+Δt, as shown at block 910, is input to block 920 to produce the actuation signal $u_D(t+\Delta t)$ through the relationship of Equation (33). The position vector $p_D(t+\Delta t)$ is delayed by an amount Δt through delay unit 915 to produce the position vector $p_D(t)$. The delayed position vector is used as a comparison for computing the error position as will be discussed presently.

Initially, Δt=0 and the actuation signal $u_D(t)$ is applied to the actuators as described by block 930. At the next sampling period, i.e., t+Δt (set by delay unit 935), the positions of all the objects in the microfluidic chamber 220 are determined by the sensor 730 to produce a position vector $p_T(t)$. The output of summing node 945 is the error position vector $p_E(t)=p_T(t)-p_D(t)$. The error position vector is applied to the dynamic gain block 950 to produce the error actuation signal for the next sample period, $u_E(t+\Delta t)$. The error actuation signal is applied to the desired actuation signal in subsequent operations to produce the total actuation signal $u_T(t+\Delta t)$, which is applied to the actuation block 930.

Figure 10:
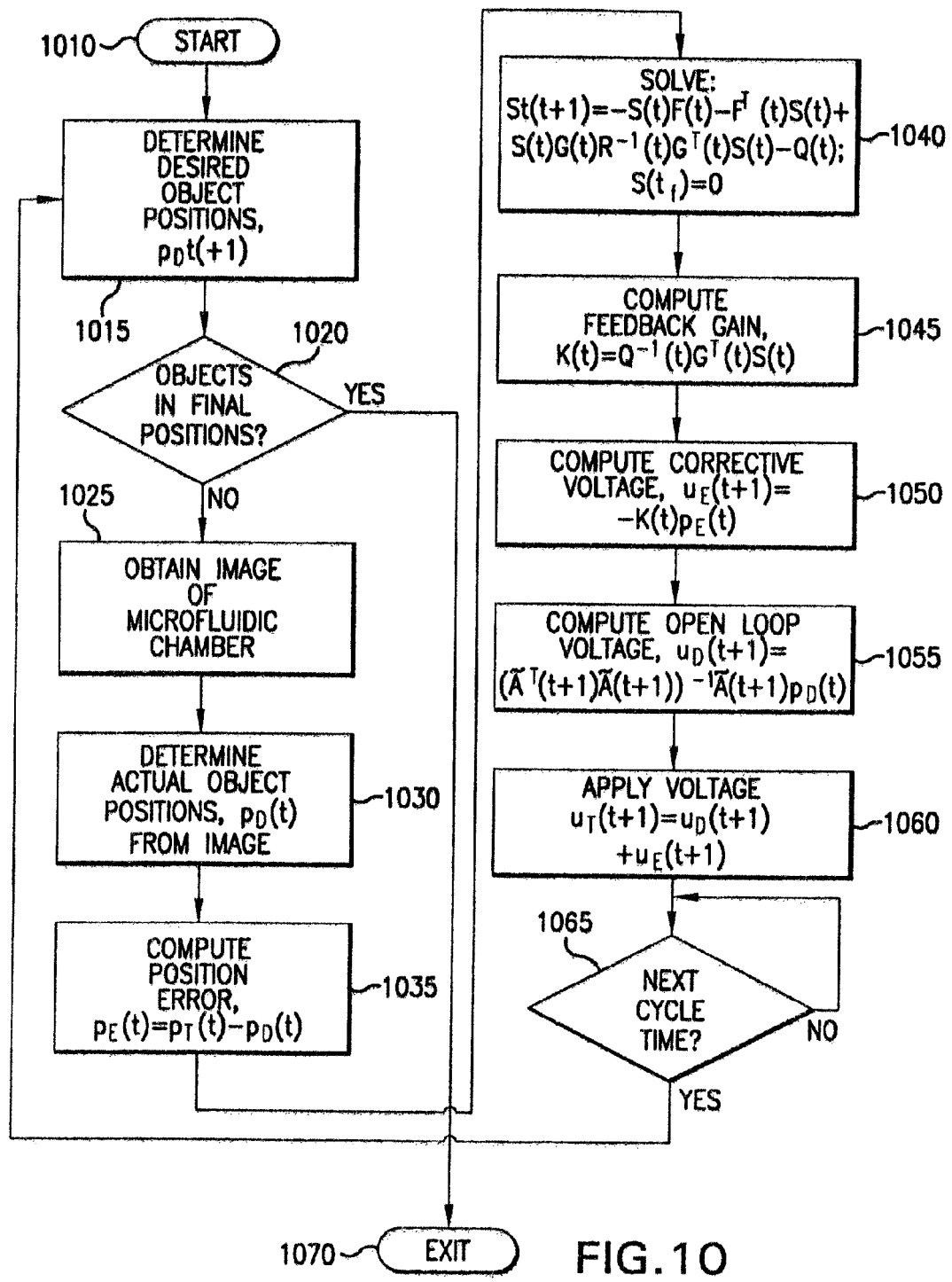
FIG. 10 is a flow chart of an exemplary embodiment of the method of the present invention.
Figure 11A:
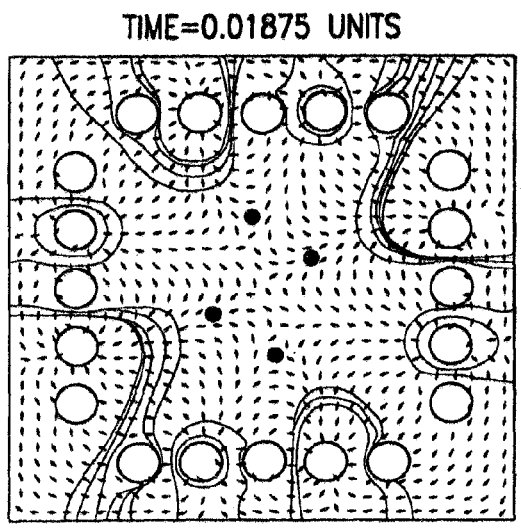
FIGS. 11A-11D are illustrations depicting motion of a plurality of particles as conducted by the method of the present invention.
Figure 11B:
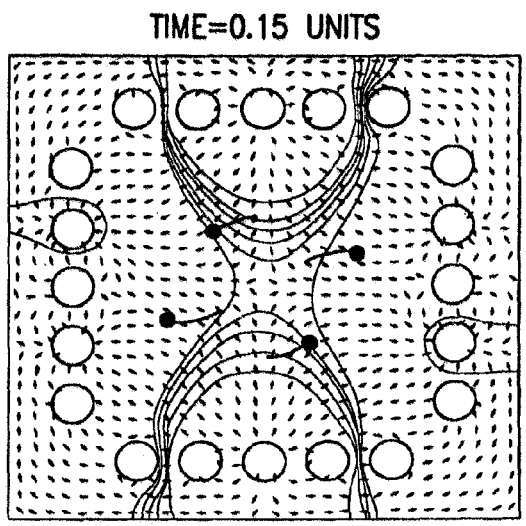
Figure 11C:
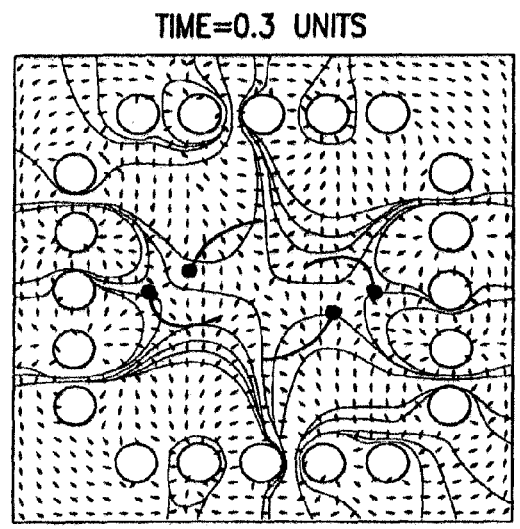
Figure 11D:
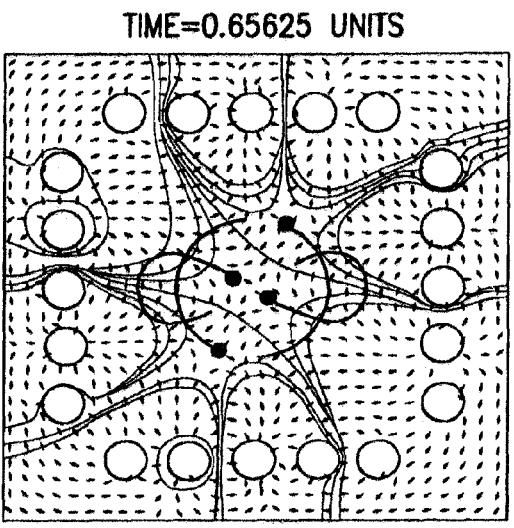

Referring now to FIG. 10, there is shown a flow chart of the principal steps of exemplary embodiments of the method of the present invention. Upon instantiation of the process at start block 1010, flow is transferred to block 1015 wherein the desired positions of objects within the microfluidic chamber 220 are determined either from a precalculated table or by dynamic computation. It is then determined, at decision block 1020, whether the objects are in the final destination and, if so, the method is terminated at exit block 1070. If it is determined that the objects are not in their respective final positions, flow is transferred to block 1025 by which an image of the microfluidic chamber 220 is captured by sensor 730. At block 1030, the actual object positions are determined by image processing, as shown at block 1030. The positional error of each of the objects is determined at block 1035.

At block 1040, the Ricatti differential equation is solved for S(t). In certain embodiments of the present invention, such as when the object trajectories have been precalculated prior to the instantiation of the method, the solution for S(t) may be determined off-line and stored for each of a plurality of predetermined regions of microfluidic chamber 220. The regions for which S(t) are solved are determined in accordance with its adjacency to each object trajectory.

Once a solution for the Ricatti differential equation has been computed in block 1040, flow is transferred to block 1045 in which the feedback gain K(t) is computed. Once again, values for K(t) may be computed off-line when the object trajectories were predetermined.

In block 1050, a corrective actuation signal is computed from the positional error of each object and, in block 1055, an open loop actuation signal is determined from the desired object position. It should be clear to one of ordinary skill in the art, that the order in which the corrective voltage and the open loop voltage are computed does not affect the outcome of the method of the present invention.

As shown at block 1060, the total actuation signal is computed as the sum of the open loop actuation signal and the corrective actuation signal and is applied to the actuators of the microfluidic device. Flow is transferred to block 1065 at which it is determined if the next sample period has arrived. If not, the method is suspended until the next sample period. Once the next cycle time has arrived, the method repeats at block 1015 until each object is in its final position as determined at block 1020.

FIGS. 11A-11D illustrate, in time sequence, the motion of four particles within the exemplary electro-osmotic microfluidic device described above. In each figure, the arrows indicate a fluid flow vector associated with the sum of eigenmodes applied to the device and the isobars indicate levels of constant pressure. As is illustrated in the Figures, motion of the four particles may be independently controlled via the underlying current flow of the fluid in the microfluidic chamber 220.

Figure 14:
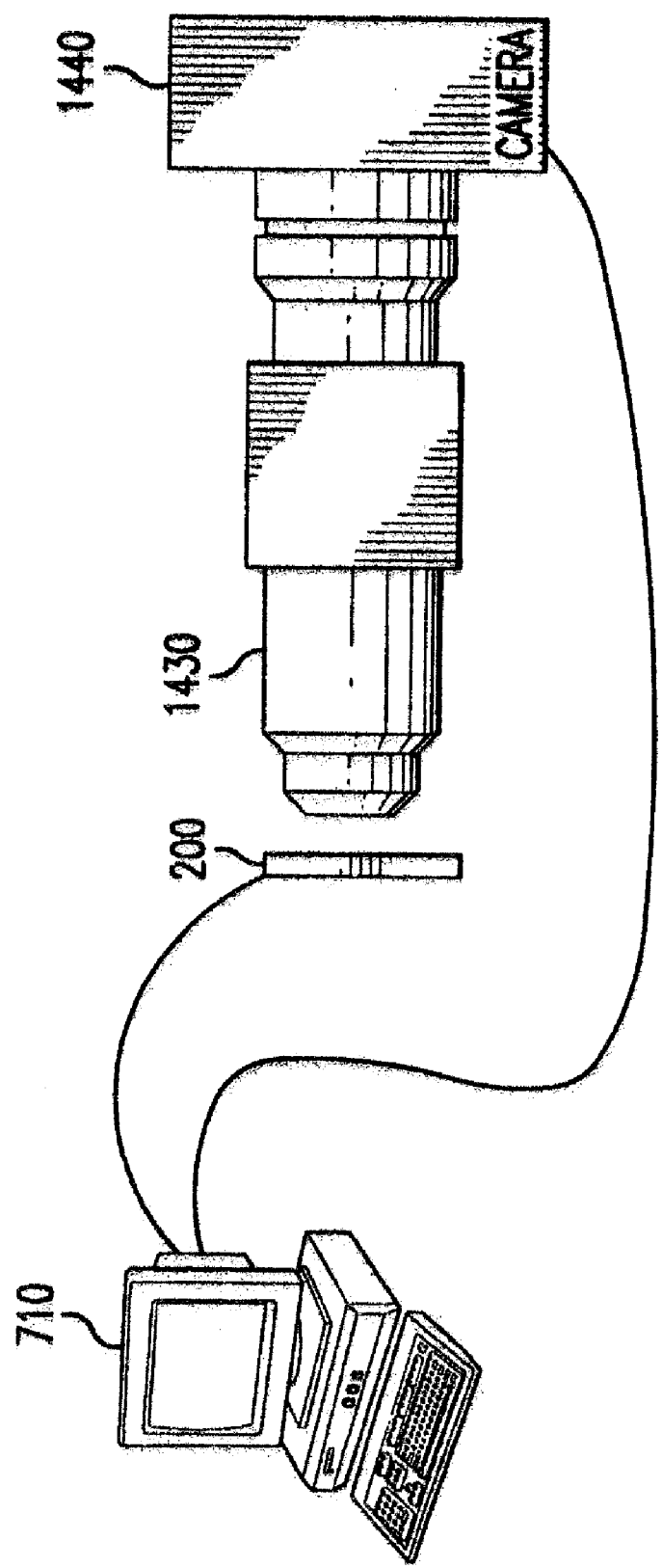
FIG. 14 is an illustration of a system configuration whereby a microscope is implemented as the sensing means for an exemplary embodiment of the present invention.

Referring now to FIG. 14, there is shown an exemplary sensing system for implementing certain embodiments of the present invention. As is shown in the Figure, a digital camera 1440 is optically coupled to a microscope 1430 at the ocular port thereof. The microscope 1430 is focused on the microfluidic chamber of microfluidic device 200. The camera/microscope serves as image capturing, system for the sensor. Subsequent image processing may configure the sensor as a position sensor for locating the positions of objects in the microfluidic device 200, as an object recognition sensor for distinguishing objects having different attributes from one another, as an object conformation sensor for determining the conformation of an object, and as an object distribution sensor for determining the positions of different segments of distributed objects. Other characteristics of objects may be ascertained as determined by the image processing technique deployed. The sensor is coupled to computer 710 which supplies the actuation signal determined from the output of the sensor as discussed hereinabove.

In certain embodiments of the present invention, an image captured by camera 1440 is passed through a threshold filter to convert the image to a binary form. As is shown in FIG. 15, a histogram of image pixel values is maintained over time and a center value is chosen for a threshold, thr. The center may be found by simple means, such as by finding a numerical average between minimum and maximum values in the histogram, or may be found by more complex statistical analysis. The binary image output by the threshold filter contains a one (1), for example, at pixel locations where the original pixel value is above the threshold value and a zero (0), for example, at pixel locations where the original pixel value is below the threshold value.

As shown in FIG. 16, the binary image produced by the threshold filter consists of binary-valued pixels. In order to process the image with sufficient speed so as to control the objects in near real-time, certain embodiments of the present invention converts the image to a run length code (RLC) representation thereof, such as is well known in the art. The RLC representation reduces significantly the data that requires further processing. The RLC for an image consists of a series of number pairs. The first number of the pair indicates the column in which an image bit is set and the second number indicates how many consecutive image bits in the current row from the current image position are set. For example, the RLC for the image of FIG. 16 may be given by the series (3,4), (2, 6), ((1, 2), (7, 2)), ((1, 2), (7, 2)), (2, 6), (3, 4).

Figure 18:
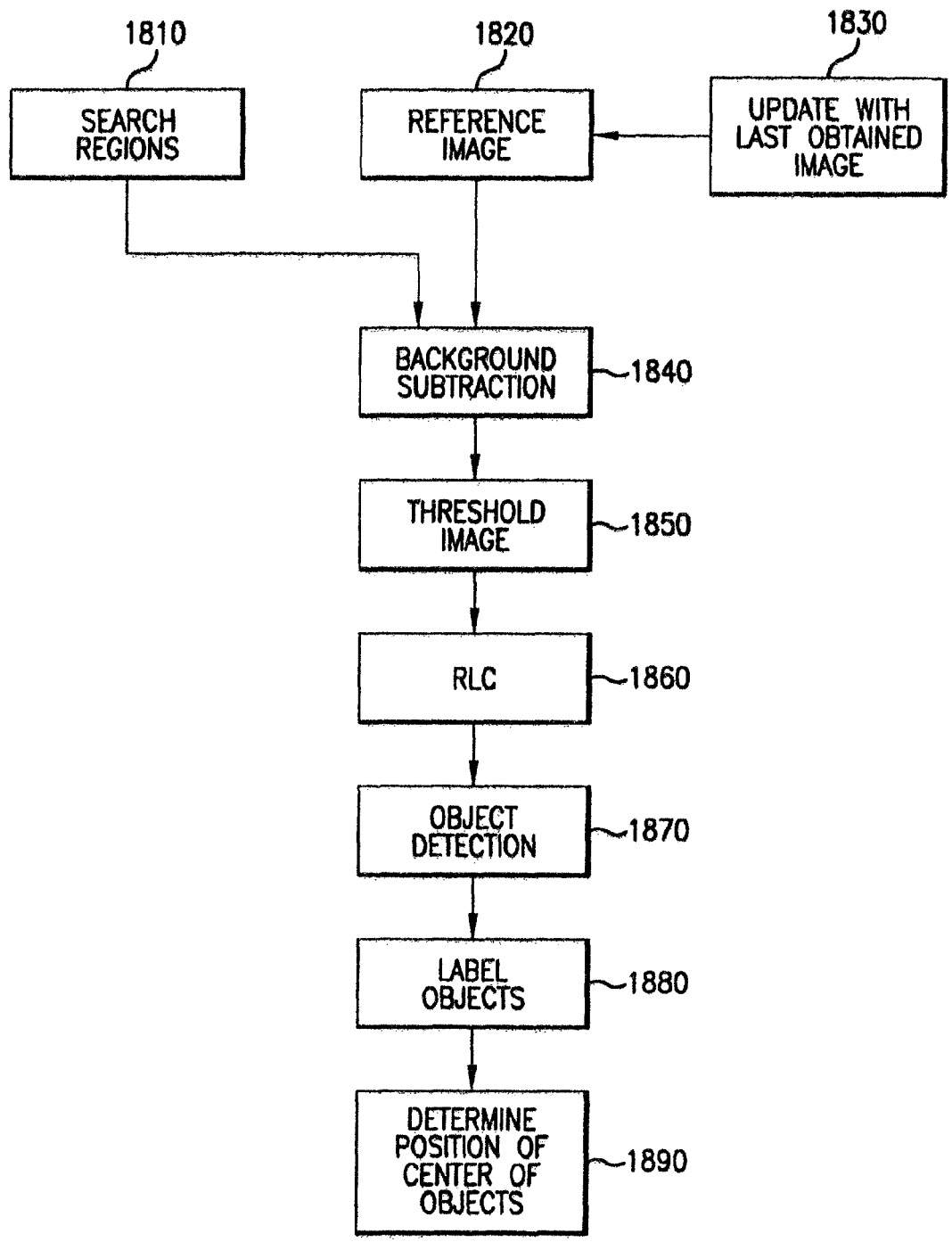
FIG. 18 is a flow chart depicting pertinent steps in an object detection process of exemplary embodiments of the present invention.

An exemplary image processing method is illustrated by way of the flow chart of FIG. 18. In block 1810, image regions of a present image in which objects are to be located are identified. This may be achieved by predictive techniques or may be accomplished by simple block processing known in the art. A previously obtained image is recalled in block 1830 and supplied to produce reference image 1820. The reference image 1820, in certain embodiments, is predicted from the previously obtained image to provide an estimate of the present image. The present image and the reference image are subtracted, as indicated at block 1840, to produce a differential image in which areas of greater difference are lighter than those areas of lesser difference. The differential image is passed through a threshold filter, such as described above, as shown at block 1850. The resulting binary image is converted to an RLC representation thereof, as shown at block 1860 and objects are detected at block 1870. The position and characteristics of ring objects as detected within a microfluidic chamber is shown in FIG. 17.

Once the objects have been detected, they may be identified and distinguished from one another by attribute. Each object may then be labeled, as shown at block 1880, by attribute or as an object previously identified, such as for purposes of object tracking. The positions of the center of the objects are identified in block 1890 and are transmitted to the object control algorithm. The object position may be determined by known techniques in the image processing art.

By way of the method of the present invention, operations on several different types of objects may be accomplished, as shown in FIGS. 12a-12d. FIG. 12a illustrates a sorting operation by which a variety of objects are sorted to corresponding sorting bin locations 1210a-1210d. In FIG. 12B, there is illustrated an example of the method of the present invention used to steer a pair of particles into one another. In FIG. 12C, an amount of fluid comprising 18% of a total amount of fluid is separated from a volume of fluid. This is accomplished by segmenting the fluid boundaries into discrete object locations, such as 1230 and 1235, and directing those locations toward each other as shown. Thus, the objects being manipulated by the present invention need not necessarily be distinct, but may be a segment of a larger structure. In like manner, FIG. 12D illustrates manipulation of stranded structures, such as DNA chains. The strand is segmented into a plurality of segment objects 1240a-1240j and the objects are conducted along trajectories to conform the strand as needed.

Figure 13A:
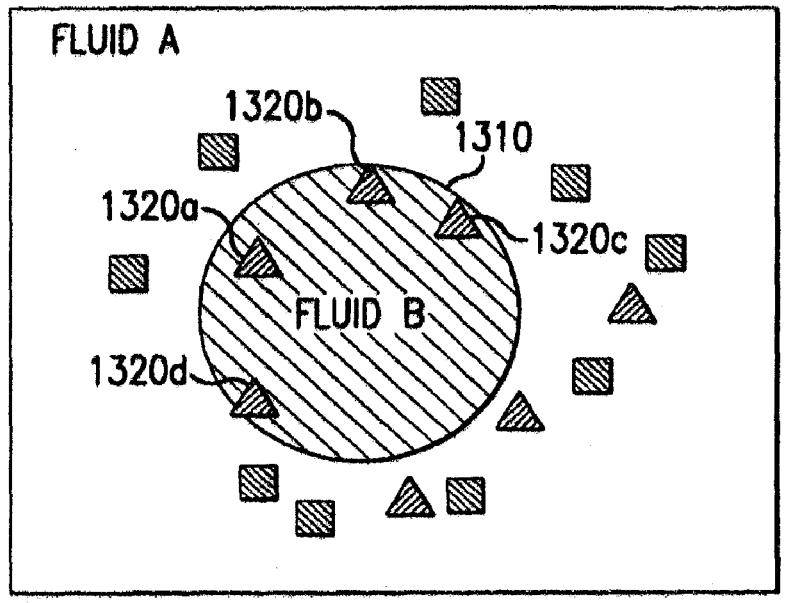
FIGS. 13A-13B illustrate an exemplary fluid distribution experiment as implemented by the method of the present invention.
Figure 13B:
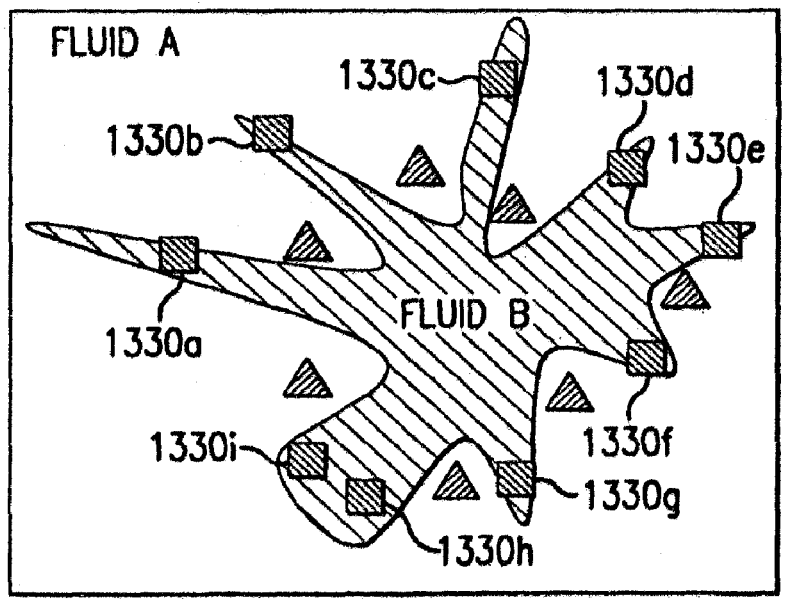

FIGS. 13A and 13B illustrate a particular example of an experiment that might be conducted by means of the present invention. In FIG. 13A, a fluid B, located at 1310, is surrounded by a fluid A and has suspended therein a plurality of particles 1320a-1320d. Fluid B may be chemically altered by objects 1320*a* and 1320*d*, wherein the amount of alteration is the quantity to be studied. After a predetermined period of time, it may be desired that fluid B be removed from all particles of the type of particles 1320*a*-1320*d* and to be moved to contact objects 1330*a*-1330*j*. Objects 1330*a*-1330*j* may respond to the chemicals under study. Objects 1330*a*-1330*j*, in subsequent steps, may be moved via the method of the present invention to a collection location for analysis.

Although the invention has been described herein in conjunction with specific embodiments thereof, many alternatives, modifications, and variations will be apparent to those skilled in the art. The present invention is intended to embrace all such alternatives, modifications, and variations that fall within the spirit and broad scope of the appended Claims.

What is claimed is:

1. A microfluidic receptacle for transporting at least one of a plurality of objects, suspended in a fluid contained by the microfluidic receptacle, respectively along a corresponding one of a plurality of trajectories, comprising:
   a plurality of actuators, operable to apply a corresponding force on the fluid; wherein said force produces at least one continuous fluid flow field; said fluid flow field requisite in the spatial locality of at least one of said plurality of objects for correcting deviation of said at least one of said plurality of objects from a destination point on said corresponding one of said plurality of trajectories and controlling movement of said at least one of said plurality of objects;
   an object position sensor, coupled via a feedback device to said plurality of actuators of said receptacle, operable to sense position data of said at least one of said plurality of objects.

2. The microfluidic receptacle of claim 1, wherein said object position sensor is chosen from the group consisting of an image sensor, electromagnetic sensor, and thermal sensor.

3. The microfluidic receptacle of claim 1, wherein each of said plurality of actuators is coupled to said object position sensor, and controlled by a system controller.

4. The microfluidic receptacle of claim 3, wherein said system controller comprises:
   a computer processor coupled to said plurality of actuators and said object position sensor;
   a storage device coupled to said processor;
   a user interface coupled to said processor and said storage device.

5. The microfluidic receptacle of claim 3, wherein said system controller comprises:
   a feedback controller adapted for controlling and correcting a position of said at least one of said plurality of objects.

6. A microfluidic receptacle for sorting at least one of a plurality of objects suspended in a fluid contained by the microfluidic receptacle, to a sorting destination region, comprising:
   a plurality of actuators, operable to apply a corresponding force on the fluid; wherein said force produces at least one continuous fluid flow field; said fluid flow field requisite in the spatial locality of said at least one of said plurality of objects for correcting deviation of said at least one of said plurality of objects from said sorting destination region and controlling the sorting of said at least one of said plurality of objects;
   an object recognition sensor, coupled via a feedback device to said plurality of actuators of said receptacle, operable to sense position and attribute data of said at least one of said plurality of objects;
   wherein said at least one of said plurality of objects is sorted to said destination region in said microfluidic receptacle in accordance with a corresponding attribute of said at least one of said plurality of objects, respectively.

7. The microfluidic receptacle of claim 6, wherein said object recognition sensor is chosen from the group consisting of an image sensor, electromagnetic sensor, and thermal sensor.

8. The microfluidic receptacle of claim 6, wherein each of said plurality of actuators is coupled to said object recognition sensor, and controlled by a system controller.

9. The microfluidic receptacle of claim 8, wherein said system controller comprises:
   a computer processor coupled to said plurality of actuators and said object recognition sensor;
   a storage device coupled to said processor;
   a user interface coupled to said processor and said storage device.

10. The microfluidic receptacle of claim 8, wherein said system controller comprises:
    a feedback controller adapted for controlling and correcting a position of said at least one of said plurality of objects.

11. A microfluidic receptacle system for transporting at least one of a plurality of objects suspended in a fluid contained by the microfluidic receptacle, respectively along a corresponding one of a plurality of trajectories, and sorting at least one of said plurality of objects suspended in a fluid contained by the microfluidic receptacle to a sorting destination region, comprising:
    a microfluidic receptacle;
    a plurality of actuators, operable to apply a corresponding force on the fluid; wherein said force produces at least one continuous fluid flow field; said fluid flow field requisite in the spatial locality of at least one of said plurality of objects for correcting for deviation of said at least one object from a destination point on said corresponding one of said plurality of trajectories, and correcting for deviation of said at least one of said plurality of objects from said sorting destination region, and controlling movement and sorting of said at least one of said plurality of objects;
    an object sensor, coupled via a feedback device to said plurality of actuators of said receptacle, operable to sense position and attribute data of said at least one of said plurality of objects;
    a system controller comprising:
      a computer processor coupled to said plurality of actuators and said object sensor;
      a storage medium coupled to said processor;
      a user interface coupled to said processor and said storage device; wherein the transporting is respectively along said corresponding one of a plurality of trajectories; wherein said at least one of said plurality of objects is sorted to said destination region in said microfluidic receptacle in accordance with a corresponding attribute of said at least one of said plurality of objects, respectively.

12. The system according to claim 11, wherein said object sensor is chosen from the group consisting of an image sensor, electromagnetic sensor, and thermal sensor.

13. The system according to claim 11, wherein said system controller further comprises:
    a feedback controller adapted for controlling and correcting a position of said at least one of said plurality of objects.

14. A microfluidic receptacle for transporting at least one of a plurality of objects, suspended in a fluid contained by the microfluidic receptacle, respectively along a corresponding one of a plurality of trajectories, comprising:
- a plurality of actuators, operable to apply a corresponding force on at least one of said plurality of objects, wherein said force produces at least one continuous force field, said force field requisite in the special locality of at least one of said plurality of objects for correcting deviation of said at least one of said plurality of objects from a destination point on said corresponding one of said plurality of trajectories, and for controlling the movement of said at least one of said plurality of said objects;
- an object position sensor, coupled via a feedback device to said plurality of actuators of said receptacle, operable to sense position data of said at least one of said plurality of objects.

15. The microfluidic receptacle of claim 14, wherein said object position sensor is chosen from the group consisting of an image sensor, electromagnetic sensor, and thermal sensor.

16. The microfluidic receptacle of claim 14, wherein each of said plurality of actuators is coupled to said object position sensor, and controlled by a system controller.

17. The microfluidic receptacle of claim 16, wherein said system controller comprises:
- a computer processor coupled to said plurality of actuators and said object position sensor;
- a storage device coupled to said processor;
- a user interface coupled to said processor and said storage device.

18. The microfluidic receptacle of claim 16, wherein said system controller comprises:
- a feedback controller adapted for controlling and correcting a position of said at least one of said plurality of objects.

19. A microfluidic receptacle for sorting at least one of a plurality of objects, suspended in a fluid contained by the microfluidic receptacle, to a sorting destination region, comprising:
- a plurality of actuators, operable to apply a corresponding force on said at least one of said plurality of objects, wherein said force produces at least one continuous force field, said force field requisite in the special locality of at least one of said plurality of objects for correcting for deviation of said at least one of said plurality of objects from said sorting destination region, and controlling the sorting of said at least one of said plurality of objects;
- an object recognition sensor, coupled via a feedback device to said plurality of actuators of said receptacle, operable to sense position and attribute data of said at least one of said plurality of objects;
- wherein said at least one of said plurality of objects is sorted to said sorting destination region in said microfluidic receptacle in accordance with a corresponding attribute of said at least one of said plurality of objects, respectively.

20. The microfluidic receptacle of claim 19, wherein said object recognition sensor is chosen from the group consisting of an image sensor, electromagnetic sensor, and thermal sensor.

21. The microfluidic receptacle of claim 19, wherein each of said plurality of actuators is coupled to said object recognition sensor, and controlled by a system controller.

22. The microfluidic receptacle of claim 21, wherein said system controller comprises:
- a computer processor coupled to said plurality of actuators and said object recognition sensor;
- a storage device coupled to said processor;
- a user interface coupled to said processor and said storage device.

23. The microfluidic receptacle of claim 21, wherein said system controller comprises:
- a feedback controller adapted for controlling and correcting a position of said at least one of said plurality of objects.

24. A microfluidic receptacle system for transporting at least one of a plurality of objects suspended in a fluid contained by the microfluidic receptacle, respectively along a corresponding one of a plurality of trajectories, and sorting at least one of said plurality of objects suspended in a fluid contained by the microfluidic receptacle to a sorting destination region, comprising:
- a microfluidic receptacle;
- a plurality of actuators, operable to apply a corresponding force on at least one of said plurality of objects, wherein said force produces at least one continuous force field, said force field requisite in the special locality of at least one of said plurality of objects for correcting for deviation of said at least one of said plurality of objects from said destination point on said corresponding one of said plurality of trajectories, correcting for deviation of said at least one of said plurality of objects from said sorting destination region, and controlling the movement and sorting of said at least one of said plurality of said objects;
- an object sensor, coupled via a feedback device to said plurality of actuators of said receptacle, operable to sense position and attribute data of said at least one of said plurality of objects;
- a system controller comprising:
  - a computer processor coupled to said plurality of actuators and said object sensor;
  - a storage medium coupled to said processor;
  - a user interface coupled to said processor and said storage device; wherein the transporting is respectively along said corresponding one of a plurality of trajectories; wherein each of said plurality of objects is sorted to said sorting destination region in said microfluidic receptacle in accordance with a corresponding attribute of each of said plurality of objects, respectively.

25. The system according to claim 24, wherein said object sensor is chosen from the group consisting of an image sensor, electromagnetic sensor, and thermal sensor.

26. The system according to claim 24, wherein said system controller further comprises:
- a feedback controller adapted for controlling and correcting a position of said at least one of said plurality of objects.

* * * * *